United States Patent
Balatero et al.

(10) Patent No.: US 9,924,648 B2
(45) Date of Patent: Mar. 27, 2018

(54) PAPAYA PLANTS HAVING A MUTANT ALLELE FOR HERMAPHRODITISM

(71) Applicant: HORTIGENETICS RESEARCH (S.E. ASIA) LTD., Chiang Mai (TH)

(72) Inventors: Conrado H. Balatero, Laguna (PH); Lamai Yapanan, Chiang Mai (TH); Katherine S. Panergayo, Lipa (PH)

(73) Assignee: HORTIGENETICS RESEARCH (S.E. ASIA) LTD., Chiang Mai (TH)

( * ) Notice: Subject to any disclaimer, the term of this patent is extended or adjusted under 35 U.S.C. 154(b) by 259 days.

(21) Appl. No.: 14/246,237

(22) Filed: Apr. 7, 2014

(65) Prior Publication Data

US 2014/0237678 A1 Aug. 21, 2014

(51) Int. Cl.
*A01H 5/08* (2018.01)

(52) U.S. Cl.
CPC ...................... *A01H 5/08* (2013.01)

(58) Field of Classification Search
None
See application file for complete search history.

(56) References Cited

U.S. PATENT DOCUMENTS 7,034,207 B2 * 4/2006 Chiu .................. A01H 5/08
435/410

FOREIGN PATENT DOCUMENTS

| AU | 2015201299 | 10/2015 |
| JP | 2015-054384 | 11/2015 |
| JP | 6071081 | 2/2017 |

OTHER PUBLICATIONS

Li et al (1994, Cereal Chem. 71(1):87-90).*
Cahoon1 (2000, PVP Certificate #9900268).*
Cahoon2 (2000, PVP Certificate #9900270).*
Awada, M. 1958. Relationship of minimum temperature and growth rate with sex expression of papaya plants (*Carica papaya* L.). Hawaii Agric. Expt. Stn. Bull. 38. 16 pp.
Chan-Tai, C., et. al. 2003. All hermaphrodite progeny are derived by self-pollinating the Sunrise papaya mutant. Plant Breed. 122:431-434.
Deputy, J.C., et. al. 2002. Molecular markers for sex determination in papaya (*Carica papaya* L.). Theor. Appl. Genet. 106:107-11.
Hofmeyr, J.D.J. 1938. Genetic studies of Carica papaya L.I. The inheritance and relation of sex and certain plant characteristics. II. Sex reversal and sex forms. South African Department of Agriculture and Science Bulletin No. 187.
Lange, A.H. 1961. Factors affecting sex changes in the flowers of *Carica* papaya L. Amer. Soc. Hort. Sci. Proc. 77:252-264.
Ming et. al. 2008. The draft genome of the transgenic tropical fruit tree papaya (*Carica papaya* Linnaeus). Nature 452, 991-996.
Morton, J. 1987. Papaya. In: Fruits of warm climates. Julia F. Morton (Ed.) Miami, Florida pp. 336-346.
Parasnis, A.S., et. al. 1999. Microsatellite (GATA)n reveals sex-specific differences in papaya. Theor. Appl. Genet. 99:1047-52.
Parasnis, A.S., et. al. 2000. A highly reliable sex diagnostic PCR assay for mass screening of papaya seedlings. Mol. Breeding 6:337-44.
Storey, W.B. 1938. Segregation of sex types in Solo papaya and their application to the selection of seed. Proc. Am. Soc Hortic. Sci. 35:83-85.
Storey, W.B. 1953. Genetics of papaya. J. Heredity 44:70-78.
Storey, W.B. 1969. Papaya. *Carica papaya* L. In: Outlines of perennial crop breeding in the tropics. Edited by Ferwerda and Wit.
Urasaki, N., et. al. 2002. A male and hermaphrodite specific RAPD marker for papaya (*Carica papaya* L). Theor. Appl. Genet. 104:281-5.
Wang et. al. 2012. Sequencing papaya X and $Y^h$ chromosomes reveals molecular basis of incipient sex chromosome evolution. Proceedings of the National Academy of Sciences 34:13710-13715.

* cited by examiner

*Primary Examiner* — Eileen B O Hara
(74) *Attorney, Agent, or Firm* — Jondle & Associates, P.C.

(57) ABSTRACT

*Papaya* plants containing mutant allele EWSMHP, which confers production of highly hermaphroditic progenies upon selfing of its hermaphrodite plants and also production of highly hermaphroditic $F_1$ progenies when crossed with normal female and normal hermaphrodite *papaya* plants, are disclosed. The invention relates to the seeds of *papaya* plants having mutant allele EWSMHP, to the plants and plant parts of *papaya* plants having mutant allele EWSMHP and to methods for producing progeny of *papaya* plants having mutant allele EWSMHP. The invention also relates to methods for producing a *papaya* plant having mutant allele EWSMHP containing in its genetic material one or more transgenes and to the transgenic *papaya* plants and plant parts produced by those methods. The invention also relates to *papaya* cultivars or breeding cultivars, and plant parts derived from *papaya* plants having mutant allele EWSMHP. The invention further relates to hybrid *papaya* seeds, plants, and plant parts produced by crossing a plant having mutant allele EWSMHP with another *papaya* cultivar.

22 Claims, No Drawings

PAPAYA PLANTS HAVING A MUTANT ALLELE FOR HERMAPHRODITISM

BACKGROUND OF THE INVENTION

The present invention relates to *papaya* plants and plant parts having a mutant allele designated EWSMHP, which confers production of highly hermaphroditic progenies upon selfing of its hermaphrodite plants and also production of highly hermaphroditic $F_1$ progenies when crossed with normal female and normal hermaphrodite *papaya* plants. Further, the present invention relates to *papaya* cultivar EWS-2499m having mutant allele EWSMHP. All publications cited in this application are herein incorporated by reference.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possesses the traits to meet the program goals. The goal is to combine in a single variety an improved combination of desirable traits from the parental germplasm. These important traits may include but are not limited to higher fruit yield, seed yield, resistance to diseases and insects, better stems and roots, tolerance to drought and heat, altered fatty acid profile, abiotic stress tolerance, improvements in compositional traits, and better agronomic quality.

These processes, which lead to the final step of marketing and distribution, can take from eight to fifteen years in *papaya* over a sufficient number of generations and with careful attention to uniformity and selection of plant type and traits. Therefore, development of new cultivars is a time-consuming process that requires precise forward planning, efficient use of resources, a minimum of changes in direction, and time for the self-selection of uniformity and traits over numerous generations.

*Papaya* (*Carica papaya* L.) is an important fruit tree commodity in many tropical and sub-tropical countries, including many countries in Southeast Asia (Thailand, Philippines, Vietnam, Indonesia) and South Asia (India, Sri Lanka, Bangladesh), Central America (Brazil, Mexico, Ecuador, Colombia) and Africa (Nigeria, Ethiopia, Kenya). *Papaya*, however, is believed to be native of tropical America (Morton, 1987). *Papaya* thrives best in areas with a temperature range of 21-33° C. and grows best in light, well-drained soils rich in organic matter (Prosea).

*Papaya* has a very unique sex expression. *Papaya* is a polygamous plant species with generally three (3) primary sex types: 1) staminate (male); 2. hermaphrodite (bisexual); and 3. pistillate (female). The male flowers are characterized by long, pendulous, freely-branching inflorescences consisting of either exclusively or predominantly staminate flowers. Female trees have short inflorescences usually consisting of only five or six flowers that are pistillate exclusively, 3-5.5 cm long with yellowish green cup-shaped calyx. Hermaphrodite trees have relatively short, few-flowered inflorescences consisting mainly of bisexual flowers.

In many countries, *papaya* growers prefer to grow only the hermaphrodite plants since hermaphrodite plants produce long cylindrical fruits which are preferred by traders and consumers. Female plants produce mostly round fruits with bigger seed cavity and hence, less ideal for transport due to its rounder shape. Most *papaya* growers plant 3 or more seedlings per hill and during flower initiation, all female trees are cut leaving only 1 hermaphrodite plant per hill. This system requires more seeds and since 3 or more seedlings are grown initially, competition takes place and sometimes resulting in non-uniform size of trees in the later stages of crop development. Hence, a *papaya* variety that can produce high proportion of hermaphrodite trees will be preferred by *papaya* growers. The identification of a true-breeding hermaphrodite *papaya* can revolutionize *papaya* production since it will completely eliminate the planting for 3 or more plants per hill as currently practiced in countries that prefer only hermaphrodite plants.

*Papaya* has three distinct chromosomes: Y for males, $Y^h$ for hermaphrodites and X for females. Storey (1938) has illustrated the different segregation ratios observed in *papaya*. For example, selfing the hermaphrodite plants will result in a segregation of 67% hermaphrodites and 33% females. Pollinating a female flower with pollen from a hermaphrodite flower will result in progenies with a segregation of 50% females and 50% hermaphrodites. Pollinating a female flower with pollen from a male plant will result in progenies with a segregation of 50% females and 50% males. These intriguing ratios led to the hypothesis that there is a lethality gene that is linked to the Y and $Y^h$ chromosomes (Storey, 1953; 1969), such that any combination of YY, $Y^hY$ and $Y^hY^h$ genotypes will be lethal. Therefore, all male and hermaphrodite *papaya* are enforced sex heterozygotes (male=XY and hermaphrodite—$XY^h$). The segregation ratios are further illustrated in Tables 1-3 below. Table 1 shows the segregation ratios when a female *papaya* is crossed with a male *papaya*. Table 2 shows the segregation ratios when a female *papaya* is crossed with a hermaphrodite (herma) *papaya*. Table 3 shows the segregation ratios when a hermaphrodite (herma) is crossed with a hermaphrodite *papaya*.

TABLE 1

Female × Male

| Female (XX) | Male (XY) | |
| --- | --- | --- |
| | X | Y |
| X | XX (F) | XY (M) |
| X | XX (F) | XY (M) |
| Ratio: | ½ F | ½ M |
| | 50% F | 50% M |

TABLE 2

Female × Herma

| Female (XX) | Herma ($XY^h$) | |
| --- | --- | --- |
| | X | $Y^h$ |
| X | XX (F) | $XY^h$ (H) |
| X | XX (F) | $XY^h$ (H) |
| Ratio: | ½ F | ½ H |
| | 50% F | 50% H |

TABLE 3

Herma × Herma

| Herma ($XY^h$) | Herma ($XY^h$) | |
| --- | --- | --- |
| | X | $Y^h$ |
| X | XX (F) | $XY^h$ (H) |
| $Y^h$ | $XY^h$ (H) | $Y^hY^h$ (lethal) |
| Ratio: | ⅓ F | ⅔ H |
| | 33% F | 67% H |

Because of the need to detect the sex of the *papaya* plant early, the identification or development of markers associated with *papaya* sex expression was a goal for some researchers. In the 1930's, Hofmeyr (1939) discovered two morphological markers—flower color and stem color, which were linked to the sex determination locus. These two morphological markers, however, were about 24 and 40 cM away and provided very little predictive value.

The development of molecular-based techniques led to the use of PCR-based markers associated with the sex of *papaya*. In the 1990s, more research was done to develop/identify sex-linked DNA markers for determining *papaya* sex types. The first sex-linked DNA marker reported was a microsatellite containing the $(GATA)_4$ repeat (Parasnis et al., 1999). Using randomly amplified polymorphic DNA (RAPD) markers, four sequence-characterized amplified region (SCAR) markers were developed by other research groups to predict sex-types (Parasnis et al., 2000; Urasaki et al., 2002; Deputy et al 2002).

While markers provide an early detection method to determine the sex of the *papaya* plant at the very early seedling stage, the cost of running these markers routinely is high, significantly more expensive than the cost of the seed itself. Others have used in vitro technology by cloning and asexually propagating hermaphrodite plants and selling in vitro-derived *papaya* seedlings. This method ensures the planting of 100% hermaphrodite plants, but the cost of in vitro-derived *papaya* seedlings is very high and requires dedicated facility and equipment for mass propagation of hermaphrodite *papaya* plants.

Hence, a method of producing high proportion of hermaphrodite plants without using markers for sex genotyping or cloning in vitro hermaphrodite plants would be highly desirable.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary, not limiting in scope. In various embodiments, one or more of the above-described problems have been reduced or eliminated, while other embodiments are directed to other improvements.

In one aspect of the invention, there is provided a novel mutant allele designated EWSMHP derived from *Carica papaya* L. that confers the production of highly hermaphroditic progenies (90-100% hermaphroditic plants and 0-10% female plants) upon selfing of hermaphrodite plants containing mutant allele EWSMHP, and highly hermaphroditic $F_1$ progenies (90-100% hermaphroditic plants and 0-10% female plants) when hermaphrodite plants containing mutant allele EWSMHP are crossed as pollen parent to a normal female *papaya*. The present invention relates to plants, seeds, fruits and other plant parts such as pollen and ovules containing mutant allele EWSMHP. The present invention further relates to methods for producing *papaya* varieties with 90-100% hermaphrodite plants by crossing *papaya* plants containing mutant allele EWSMHP with itself or with another *papaya* variety, and the creation of variants by mutagenesis or transformation of *papaya* plants containing mutant allele EWSMHP. The invention further relates to *papaya* plants produced by said methods.

According to the invention, there is provided a new *papaya* cultivar designated EWS-2499m containing mutant allele EWSMHP. This invention thus relates to the seeds of *papaya* cultivar EWS-2499m, to the plants and plant parts of *papaya* cultivar EWS-2499m, and to methods for producing a *papaya* plant by grafting *papaya* cultivar EWS-2499m to a rootstock of another variety, to crossing *papaya* cultivar EWS-2499m with itself or another *papaya* cultivar, the creation of variants by mutagenesis, cell culture, transformation of *papaya* cultivar EWS-2499m or other methods of transference of EWS-2499m genetic material, traits or attributes, and to methods of producing open-pollinated and $F_1$ hybrids of *papaya* that will give more than 90% hermaphrodite progenies using *papaya* cultivar EWS-2499m as a parent.

This invention also relates to methods for introgressing a transgenic or mutant trait into *papaya* cultivar EWS-2499m and to the *papaya* plants and plant parts produced by those methods. This invention also relates to *papaya* cultivars or breeding cultivars and plant parts derived from *papaya* cultivar EWS-2499m, to methods for producing other *papaya* cultivars or plant parts derived from *papaya* cultivar EWS-2499m and to the *papaya* plants, varieties, and their parts derived from the use of those methods. This invention further relates to *papaya* seeds, plants, and plant parts produced by crossing *papaya* cultivar EWS-2499m with another *papaya* cultivar. Thus, any such methods existing now or in the future of using the *papaya* cultivar EWS-2499m are part of this invention including but not limited to: selfing, backcrosses, hybrid production, crosses to populations, stem cells and the like. All plants produced using *papaya* cultivar EWS-2499m or *papaya* plants derived from crosses with EWS-2499m or *papaya* plants containing the EWSMHP allele are within the scope of this invention. Advantageously, the *papaya* cultivar could be used in crosses with other, different, *papaya* plants to produce first generation ($F_1$) *papaya* hybrid seeds and plants with superior characteristics.

In another aspect, the present invention provides regenerable cells for use in tissue culture or stem cells of *papaya* cultivar EWS-2499m. The tissue culture or stem cells will preferably be capable of regenerating plants having all the physiological and morphological characteristics of the foregoing *papaya* plant, and of regenerating plants having substantially the same genotype as the foregoing *papaya* plant. Preferably, the regenerable cells in such tissue cultures will be embryos, protoplasts, meristematic cells, callus, pollen, leaves, ovules, anthers, cotyledons, hypocotyl, pistils, roots, root tips, flowers, seeds, petiole, pods, fruit or stems. Still further, the present invention provides *papaya* plants regenerated from the tissue cultures, stem cells or other means of genomic transfer of the invention.

In addition to the exemplary aspects and embodiments described above, further aspects and embodiments will become apparent by study of the following descriptions in conjunction with the accompanying tabular data; and, it is to be expressly understood that these descriptions and data are for the purpose of illustration and/or description and is not intended as a definition of the limits of the invention.

DETAILED DESCRIPTION OF THE INVENTION

In the description and tables that follow, a number of terms are used. In order to provide a clear and consistent understanding of the specification and claims, including the scope to be given such terms, the following definitions are provided:

Abiotic stress. As used herein, abiotic stress relates to all non-living chemical and physical factors in the environment.

Examples of abiotic stress include, but are not limited to, drought, flooding, salinity, pH, nutritional requirements, light-dark requirements, $CO_2$ requirements, temperature, and climate change.

Allele. Any of one or more alternative forms of a genetic sequence. In a diploid cell or organism, the two alleles of a given sequence typically occupy corresponding loci on a pair of homologous chromosomes.

Alter. The utilization of up-regulation, down-regulation, or gene silencing or splicing/insertion/deletions.

Backcrossing. A process in which a breeder crosses progeny back to one of the parental genotypes one or more times. Commonly used to introduce one or more locus conversions from one genetic background into another.

Breeding. The genetic manipulation of living organisms or cells.

Cell. Cell as used herein includes a plant cell, whether isolated, in tissue culture or incorporated in a plant or plant part.

Cell culture. Cell or "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, petioles, leaves, stems, roots, root tips, anthers, pistils, and the like.

Commodity plant product. Products that are wholly derived from a EWS-2499m plant or part thereof or a product that contains one or more ingredients derived from a EWS-2499m plant or part thereof. Commodity plant products include, but are not limited to, papain, meat tenderizers, anti-oxidants, candies, preserved fruits, tea, beauty or cosmetic products such as shampoo, lotion, soap, beauty creams and make-up, flavonoids, fuels, juice, pulp, peel, seed, protein isolates, protein concentrates, vinegars, alcohols, medicines, deodorants, plastics, enzymes, jellied sauces and honeys.

Cotyledon. A cotyledon is a type of seed leaf. The cotyledon contains the food storage tissues of the seed.

Cross-pollination. Fertilization by the union of two gametes from different plants.

Diploid. A cell or organism having two sets of chromosomes.

Embryo. The embryo is the small plant contained within a mature seed.

EWSMHP. The *papaya* mutant allele of the present invention. The EWSMHP mutant allele results in highly hermaphroditic plant progenies (90-100% hermaphroditic plants and 0-10% female plants) upon selfing of hermaphrodite plants containing mutant allele EWSMHP, and results in highly hermaphroditic $F_1$ plant progenies (90-100% hermaphroditic plants and 0-10% female plants) when hermaphrodite plants containing mutant allele EWSMHP are crossed as pollen parent to a normal female *papaya*. *Papaya* cultivar EWS-2499m contains mutant allele EWSMHP.

$F_\#$. The "F" symbol denotes the filial generation, and the # is the generation number, such as $F_1$, $F_2$, $F_3$, etc.

Gene. As used herein, "gene" refers to a unit of inheritance corresponding to DNA or RNA that code for a type of protein or for an RNA chain or at times certain proteins that has a function in the organism.

Gene silencing. The interruption or suppression of the expression of a gene at the level of transcription or translation or through the introduction of plasmids.

Genotype. Refers to the genetic constitution of a cell or organism.

Grafting. A bud, shoot, or scion of a plant inserted in a groove, slit, or the like in a stem or stock of another plant in which it continues to grow or the plant resulting from such an operation or the united stock and scion or the place where the scion is inserted.

Haploid. A cell or organism having one set of the two sets of chromosomes in a diploid.

Highly hermaphroditic plant progenies. As used herein, indicates 90-100% hermaphroditic plants and 0-10% female plants.

Hypocotyl. A hypocotyl is the portion of an embryo or seedling between the cotyledons and the root. Therefore, it can be considered a transition zone between shoot and root.

Linkage. Refers to a phenomenon wherein alleles on the same chromosome tend to segregate together more often than expected by chance if their transmission was independent.

Linkage disequilibrium. Refers to a phenomenon wherein alleles tend to remain together in linkage groups when segregating from parents to offspring, with a greater frequency than expected from their individual frequencies.

Locus. A defined segment of DNA.

Nucleic acid. An acidic, chainlike biological macromolecule consisting of multiple repeat units of phosphoric acid, sugar and purine and pyrimidine bases.

*Papaya* ringspot virus (PRSV). A pathogenic plant virus in the genus *Potyvirus* and the virus family Potyviridae that infects *papaya*.

Pedigree. Refers to the lineage or genealogical descent of a plant.

Pedigree distance. Relationship among generations based on their ancestral links as evidenced in pedigrees. May be measured by the distance of the pedigree from a given starting point in the ancestry.

Percent identity. Percent identity as used herein refers to the comparison of the homozygous alleles of two *papaya* varieties. Percent identity is determined by comparing a statistically significant number of the homozygous alleles of two developed varieties. For example, a percent identity of 90% between *papaya* variety 1 and *papaya* variety 2 means that the two varieties have the same allele at 90% of their loci.

Percent similarity. Percent similarity as used herein refers to the comparison of the homozygous alleles of a *papaya* variety such as *papaya* cultivar EWS-2499m with another plant, and if the homozygous allele of *papaya* cultivar EWS-2499m matches at least one of the alleles from the other plant, then they are scored as similar. Percent similarity is determined by comparing a statistically significant number of loci and recording the number of loci with similar alleles as a percentage. A percent similarity of 90% between *papaya* cultivar EWS-2499m and another plant means that *papaya* cultivar EWS-2499m matches at least one of the alleles of the other plant at 90% of the loci.

Pith. As used herein, the term "pith" refers to the white fleshy part of the rind.

Plant. As used herein, the term "plant" includes reference to an immature or mature whole plant, including a plant from which seed, grain, fruit, thorns or anthers have been removed. Seed, stem cells, air layering, cell culture or embryo that will produce the plant is also considered to be the plant. The term plant shall include *papaya* cultivar EWS-2499m "tree" as well.

Plant height. Plant height is taken from the top of the soil to the top node of the plant and is measured in centimeters or inches. Width of the plant is also measured in centimeters or inches.

Plant parts. As used herein, the term "plant parts" (or a *papaya* plant, or any part thereof) includes but is not limited to protoplasts, leaves, stems, roots, root tips, anthers, pistils, seed, grain, embryo, pollen, ovules, cotyledon, hypocotyl, fruit, flower, shoot, branches, tissue, petiole, cells, sap, oils, antioxidants, nutrients, "veins" of branches and/or leaves, bark, flowers as a whole or in parts, fruit as a whole or in parts, rind, pulp, stem cells, genome, meristematic cells, and the like. The term plant parts shall include *papaya* cultivar EWS-2499m "tree" or parts thereof as well.

Progeny. As used herein, includes an $F_1$ *papaya* plant produced from the cross of two *papaya* plants where at least one plant includes *papaya* cultivar EWS-2499m and progeny further includes, but is not limited to, subsequent $F_2$, $F_3$, $F_4$, $F_5$, $F_6$, $F_7$, $F_8$, $F_9$, and $F_{10}$ generational crosses.

Quantitative Trait Loci (QTL). Quantitative trait loci (QTL) refer to genetic loci that control to some degree numerically representable traits that are usually continuously distributed.

Regeneration. Regeneration refers to the development of a plant or plant parts from tissue culture, seed, air layering, grafting, cell culture, stem cells or genomic transfer.

Single gene converted (Conversion). Single gene converted (conversion), also known as coisogenic plants, refers to plants which are developed by a plant breeding technique called backcrossing wherein essentially all of the desired morphological and physiological characteristics of a variety are recovered in addition to the single gene transferred into the variety via the backcrossing technique or via genetic engineering.

Stem cells or progenitor cells. An unspecialized cell found in a plant, plant parts or adult plant tissues that has the potential to develop into specialized cells or divide into other stem cells. Stem cells can develop into any type of differentiated cells. Stem cells can potentially be used to replace tissue damaged or destroyed by disease or injury, or to produce new plants or plant parts. but the use of embryonic stem cells for this purpose is controversial.

*Papaya* mutant allele EWSMHP confers the production of highly hermaphroditic progenies (90-100% hermaphroditic plants and 0-10% female plants) upon selfing of hermaphrodite plants containing mutant allele EWSMHP, and highly hermaphroditic $F_1$ progenies (90-100% hermaphroditic plants and 0-10% female plants) when hermaphrodite plants containing mutant allele EWSMHP are crossed as pollen parent to a normal female *papaya*. Mutant allele EWSMHP of the present invention is heritable and has been transferred to many different *papaya* lines.

*Papaya* cultivar EWS-2499m is a new inbred *papaya* line containing mutant allele EWSMHP that produces highly hermaphroditic progenies (90-100%) upon selfing of its hermaphrodite plants. In contrast, selfing of a normal hermaphrodite plant will generate approximately ⅔ hermaphrodite plants and ⅓ female plants. Further, when *papaya* cultivar EWS-2499m was crossed with normal female plants, greater than 90% of the $F_1$ progenies were hermaphrodites. In contrast, the normal sex segregation between a cross of normal female *papaya* and normal hermaphrodite *papaya* plant is 1:1 (female:hermaphrodite).

*Papaya* cultivar EWS-2499m containing mutant allele EWSMHP is a highly hermaphroditic inbred line that was derived from a variable population of an East-West Seed breeding line. The present invention differs from mutant *papaya* line TSS No. 7 described by Chan-Tai et al. (U.S. Pat. No. 7,034,207) in that *papaya* cultivar EWS-2499m is derived from a completely different, morphologically distinct source than the source of Chan-Tai et al. Specifically, the *papaya* of Chan-Tai et al. was derived from Sunrise, an open-pollinated Solo *papaya* variety popular in Hawaii, whereas *papaya* cultivar EWS-2499m was derived from a segregating population of an East-West Seed breeding material. Likewise, the genetic control and expression of the highly hermaphroditic trait of EWS-2499m, designated herein as mutant allele EWSMHP, is completely different from that of Chan-Tai et al., which claimed all hermaphrodite (100%) expression of its mutant line when self-pollinated and a 1:1 segregation (50:50) of female and hermaphrodite plants when the all-hermaphroditic mutant variety TSS No. 7 is crossed with a normal female, which is similar to a cross between a normal female and a normal hermaphrodite plant as described by Storey (1938; 1953). The highly hermaphroditic line EWS-2499m of the present invention does not always result in 100% hermaphroditic expression upon selfing (instead results in 90%-100% hermaphrodite and 0-10% female) and results in highly hermaphroditic trait expression in $F_1$ progenies (90%-100% hermaphrodite and 0-10% female) using the EWS-2499m hermaphroditic line as one of the parents, which is a large contrast to the 50% hermaphrodite: 50% female segregation obtained by Chan-Tai et al (2003, 2006) when all hermaphrodite mutant line TSS No. 7 was crossed with a normal female *papaya* plant.

*Papaya* cultivar EWS-2499m is also distinguished by having intermediate resistance to the *papaya* ringspot virus (PRSV), distinctively long, slim cylindrical fruits with an average fruit length of 28.0 cm, and a deep yellow flesh color.

*Papaya* cultivar EWS-2499m has shown uniformity and stability, as described in the following variety description information. It has been self-pollinated over a sufficient number of generations and years with careful attention to uniformity of plant type and traits. The line has been increased with continued observation and selection for uniformity and traits.

*Papaya* cultivar EWS-2499m has the following morphologic and other characteristics, (based primarily on data collected in Chiangmai, Thailand), which are shown in comparison to the morphological characteristics of *papaya* line TSS No. 7 as reported in U.S. Pat. No. 7,034,207.

TABLE 4

VARIETY DESCRIPTION INFORMATION

| Characteristics | EWS-2499m | TSS No. 7 |
| --- | --- | --- |
| PLANT | | |
| Plant gender | Hermaphrodite | Hermaphrodite |
| Size: height (cm) | >200 | >150 |
| Size: diameter (cm) | 35 | 18 |
| Nodes to $1^{st}$ flower | 14-16 | 25 |
| Length between nodes (cm) | 5.2 | 2.9 |
| Height at $1^{st}$ harvest | 60-80 cm | <1.0 m |

TABLE 4-continued

VARIETY DESCRIPTION INFORMATION

| Characteristics | EWS-2499m | TSS No. 7 |
|---|---|---|
| Average fruit number/plant | 80 | 47 |
| Production (kg/year) | 88 | <50 |
| Maturity of fruit (days after transplanting) | 220-240 | 111-140 |
| Bark color | Brown | Light greyed-brown |
| Foliage density (number of leaves at the apex) | 22 | 27.8 |
| Maturity (days from pollination to harvest) | 140-150 | 113-140 |
| LEAF | | |
| Mature petiole color | Green | Green |
| Mature petiole length (cm) | 75.0 | 77.2 |
| Mature petiole diameter (cm) | 1.8 | 1.39 |
| Leaf lamina length (cm) | 55.0 | 71.1 |
| Leaf lamina width (cm) | 87.3 | 65.6 |
| Form | Lobed palmate | Shallowly lobed palmate |
| FLOWERS | | |
| Type | Hermaphrodite | Hermaphrodite |
| Color of inflorescence stalk | Light green | Light green |
| Flower number per node | 3 main, 6 secondary flowers | 1-3 |
| Size | Small-medium | Small |
| Color | White yellow | White yellow |
| FRUIT | | |
| Form | Slim, cylindrical | Pear-like shape |
| Base attached to the peduncle | Flat | Flat |
| Skin color | Yellow | Dark yellow-orange |
| Skin texture | Gritty, medium firm | Average to gritty, medium firm to firm |
| Skin thickness | Medium | Medium |
| Flesh color | Deep yellow | Orange to dark red |
| Flesh flavor | Strong | Strong |
| Flesh firmness | Moderate | Firm |
| Fibers | Present | Exist |
| Eating quality | Good | Exceptionally high |
| Seed cavity at central position | Star-shaped | Star-shaped |
| Seed cavity width at central position (cm) | 9.5 | 4.3 |
| Fruit weight (g) | 1100 | 500 |
| Fruit length (cm) | 28.0 | 14.1 |
| Fruit width (cm) | 9.8 | 8.5 |
| Brix | 10-12 degrees | 13 degrees |
| SEEDS | | |
| Color | Dark brown | Brown black |
| Shape | Round | Round or oval |
| Surface | Dark | Dark, opacity, slimy |
| Average dry weight per 100 seeds (g) | 1.4 | 0.94 |
| Average wet weight of seeds in a fruit (g) | Not determined | 29.1 |
| INSECT/PEST RESISTANCE | | |
| Red spider mites | Susceptible | Highly susceptible |
| White spider mites | Not determined | Susceptible |
| Scale | Susceptible | Susceptible |
| Nematodes | Not determined | Susceptible |
| Snails | Not determined | Susceptible |
| DISEASE RESISTANCE | | |
| Anthracnose | Susceptible | Highly susceptible |
| *Phytophthora* fruit rot | Susceptible | Highly susceptible |
| Powdery mildew | Susceptible | Highly susceptible |
| Root rot | Susceptible | Susceptible |
| Seedling blight | Susceptible | Highly susceptible |
| Stem end rot | Susceptible | Susceptible |
| Papaya ringspot virus (PRSV) | Intermediate resistance | Very highly susceptible |
| *Phytophthora palmivora* Butler | Not determined | Susceptible |
| Melanose | Not determined | Susceptible |
| Black rot | Not determined | Susceptible |

This invention is also directed to methods for producing a *papaya* plant by crossing a first parent *papaya* plant with a second parent *papaya* plant, wherein the first or second *papaya* plant is the *papaya* cultivar EWS-2499m. Further, both first and second parent *papaya* plants may be *papaya* cultivar EWS-2499m. Therefore, any methods using *papaya* cultivar EWS-2499m are part of this invention: selfing, backcrosses, hybrid breeding, and crosses to populations.

Any plants developed using *papaya* cultivar EWS-2499m and/or *papaya* lines containing the EWSMHP allele derived from EWS-2499m as a progenitor are within the scope of this invention.

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using *Agrobacterium*-mediated transformation. Transformant plants obtained with the protoplasm of the invention are intended to be within the scope of this invention.

EXAMPLES

Example 1. Development of Inbred Line EWS-2499m and Identification of Mutant Allele EWSMHP A selfed progeny from a segregating East-West Seed breeding line with yellow flesh (coded as EWS-445) was evaluated in Chiangmai, Thailand and found to be segregating for various morphological traits including plant height, plant vigor, relative resistance or susceptibility to PRSV, fruit setting, cat-face formation or carpellody and fruit gapping. Hermaphrodite individual plants were selected from this population on the basis of improved PRSV resistance, strong plant vigor, good fruit setting, less sensitivity to sex carpellody and less fruit gapping. The hermaphrodite flowers of selected individual plants were selfed by bagging the hermaphrodite flowers.

Selfing of the selected plants (hermaphrodites) was done for several generations selecting for the same desirable plant characteristics—intermediate resistance to PRSV, strong plant vigor, good fruit setting, less sensitivity to carpellody and less fruit gapping or female sterility. In addition to these characteristics, the segregation of female and hermaphrodite trees was also determined for each selected line.

After six selfing generations of EWS-445, one inbred line (EWS-445-3-0-7-6-6-3) showed a distorted segregation of the number of hermaphrodite flowers to female flowers since it produced more than 90% hermaphrodites in contrast to the expected segregation of 2:1 (herma:female) or 67% hermaphrodites and 33% females as described by Storey (1938, 1953). This inbred line (EWS-445-3-0-7-6-6-3) was given a new code EWS-2499m with "m" denoting mutation; in contrast to two other sister lines (EWS-445-3-0-7-6-6-1 and EWS-445-3-0-7-6-6-2) which showed the normal expected segregation of 2:1 (hermaphrodites to females). The two normally segregating lines were coded as EWS-2497n and EWS-2498n, respectively, with "n" denoting normal segregation. The mutant trait of EWS-2499m is designated herein as mutant allele EWSMHP. To check if the mutation is heritable, two randomly selected hermaphrodite plants of EWS-2499m (coded as EWS-2499m-1 and EWS-2499m-2) were selfed for two generations and checked for sex segregation. Likewise, randomly selected hermaphrodite plant each of EWS-2497n and EWS-2498n were also selfed for two generations for comparison.

Example 2. Segregation Patterns of Normal Hermaphrodite *Papaya* Plants Upon Selfing As described above, selfing of normal hermaphrodite *papaya* plants will result in a segregation of 67% hermaphrodites and 33% females. Normal hermaphrodite *papaya* lines EWS-2497n and EWS-2498n were selfed for two generations and the segregation of the resultant progeny was observed. As shown in Table 5, the normal hermaphrodite *papaya* lines EWS-2497n and EWS-2498n and their selfed progenies resulted in segregation ratios of between 59.8-67.1% hermaphrodite plants to 32.9-40.2% female, similar to the expected segregation ratio of 67% hermaphrodite to 33% females.

Example 3. Segregation Patterns of Hermaphrodite Plants Containing Mutant Allele EWSMHP Upon Selfing

*Papaya* cultivar EWS-2499m was selfed for two generations and the segregation patterns of the resulting progeny were observed. As shown in Table 5, selfing of EWS-2499m resulted in progeny that segregated at between 94.1-100% hermaphrodite to 0-5.9% female, indicating that the segregation patterns of *papaya* EWS-2499m are clearly different and distinct from those of a normal hermaphrodite *papaya*, which segregate at 67% hermaphrodite to 33% females.

In summary, the results of the sex segregation (females and hermaphrodites) of the selfed progenies of EWS-2497n (normal), EWS-2498n (normal) and EWS-2499m (mutant) and their succeeding selfing generations are presented in Table 5. Table 5, column 1 shows the code name, column 2 shows the location, where TH indicates Thailand and PH indicates Philippines, column 3 shows the year evaluated, column 4 shows the total number of plants that were evaluated at flowering stage, column 5 shows the number of hermaphroditic (H) progenies, column 6 shows the number of female (F) progenies, column 7 shows the percentage of hermaphroditic progenies, column 8 shows the percentage of female progenies, column 9 shows the expected segregation ratio, column 10 shows the expected percentage of hermaphroditic progenies, column 11 shows the expected percentage of female progenies, column 12 shows the chi squared value ($\chi^2$), and column 13 shows the statistical significance where '***' indicates highly significant at P<0.001, Chi-square critical value, 1 df=6.635, and 'ns' indicates not statistically significant.

TABLE 5

| | | | Progenies evaluated | | | | | Expected | | | | |
| | | | Total | | | | | segregation | | | | |
| Code | Location | Year evaluated | plants | H | F | % H | % F | Ratio | % H | % F | χ2 value | Significance |
| --- | --- | --- | --- | --- | --- | --- | --- | --- | --- | --- | --- | --- |
| | | | | Normal segregating herma lines | | | | | | | | |
| EWS-2497n | TH | 2009 | 148 | 95 | 53 | 64.2 | 35.8 | 2:1 | 66.7 | 33.3 | 0.41 | ns |
| EWS-2497n-1 | TH + PH | 2010 | 81 | 52 | 29 | 64.2 | 35.8 | 2:1 | 66.7 | 33.3 | 0.2 | ns |

TABLE 5-continued

|  |  |  | Progenies evaluated | | | | | Expected segregation | | | | |
| --- | --- | --- | --- | --- | --- | --- | --- | --- | --- | --- | --- | --- |
| Code | Location | Year evaluated | Total plants | H | F | % H | % F | Ratio | % H | % F | χ2 value | Significance |
| EWS-2497n-1-1 | TH + PH | 2012 | 101 | 66 | 35 | 65.3 | 34.7 | 2:1 | 66.7 | 33.3 | 0.1 | ns |
| EWS-2497n-1-2 | TH + PH | 2012 | 107 | 64 | 43 | 59.8 | 40.2 | 2:1 | 66.7 | 33.3 | 2.3 | ns |
| EWS-2498n | TH | 2009 | 85 | 57 | 28 | 67.1 | 32.9 | 2:1 | 66.7 | 33.3 | 0.01 | ns |
| EWS-2498n-1 | TH + PH | 2010 | 67 | 43 | 24 | 64.2 | 35.8 | 2:1 | 66.7 | 33.3 | 0.2 | ns |
| EWS-2498n-1-1 | TH + PH | 2012 | 92 | 60 | 32 | 65.2 | 34.8 | 2:1 | 66.7 | 33.3 | 0.1 | ns |
| Highly hermaphroditic mutant lines | | | | | | | | | | | | |
| EWS-2499m | TH | 2009 | 34 | 32 | 2 | 94.1 | 5.9 | 2:1 | 66.7 | 33.3 | 11.5 | *** |
|  | PH | 2009 | 56 | 54 | 2 | 96.4 | 3.6 | 2:1 | 66.7 | 33.3 | 22.3 | *** |
| EWS-2499m-1 | TH + PH | 2010 | 64 | 64 | 0 | 100.0 | 0.0 | 2:1 | 66.7 | 33.3 | 32.0 | *** |
| EWS-2499m-1-1 | TH + PH | 2012 | 101 | 95 | 6 | 94.1 | 5.9 | 2:1 | 66.7 | 33.3 | 34.1 | *** |
| EWS-2499m-2 | TH + PH | 2010 | 50 | 48 | 2 | 96.0 | 4.0 | 2:1 | 66.7 | 33.3 | 19.4 | *** |
| EWS-2499m-2-1 | TH + PH | 2012 | 118 | 115 | 3 | 97.5 | 2.5 | 2:1 | 66.7 | 33.3 | 50.3 | *** |
| EWS-2499m-2-2 | TH + PH | 2012 | 113 | 112 | 1 | 99.1 | 0.9 | 2:1 | 66.7 | 33.3 | 53.5 | *** |

As shown in Table 5, the sex segregation of hermaphrodites to female plants of EWS-2499m and its derived lines which contain mutant allele EWSMHP (EWS-2499m-1, EWS-2499m-1-1, EWS-2499m-2, EWS-2499m-2-1, EWS-2499m-2-2) upon selfing was 94.1%-100% hermaphrodite progeny, which significantly deviated from the expected segregation of ⅔ hermaphrodites to ⅓ females based on chi-square goodness of fit (p<0.001). In contrast, the segregation or ratio of hermaphrodites to female plants of normal segregating lines (EWS-2497n and EWS-2498n) which do not contain mutant allele EWSMHP and their derived lines (EWS-2497n-1, EWS-2497n-1-1, EWS-2497n-1-2, EWS-2498n-1, and EWS-2498n-1-1) upon selfing was approximately 66.7% herma: 33.3% female, was as expected based on 2:1 (hermaphrodites: females) segregation.

As shown in Table 5, selfing of the *papaya* EWS-2499m inbred line can result in a highly hermaphroditic open-pollinated variety. The mutant trait, designated herein as mutant allele EWSMHP, is heritable and can be transferred to other elite lines, hence, highly hermaphroditic open-pollinated varieties that can produce more than 90% hermaphrodites (instead of the expected 67%) can be developed using the mutant trait derived from mutant inbred *papaya* line EWS-2499m.

Example 4. Transferring Mutant Allele EWSMHP to Other Genetic Backgrounds

Unexpectedly, the novel genetic factor of the present invention, which has been designated EWSMHP, is capable of transmitting the production of highly hermaphroditic progenies (90-100% hermaphroditic plants and 0-10% female plants) upon selfing of hermaphrodite plants containing mutant allele EWSMHP, and highly hermaphroditic $F_1$ progenies (90-100% hermaphroditic plants and 0-10% female plants) when hermaphrodite plants containing mutant allele EWSMHP are crossed as pollen parent to a normal female *papaya*. Mutant allele EWSMHP is believed to be a novel dominant allele that may have additional modifier genes. It is a feature of the present invention that mutant allele EWSMHP may be used in and transferred among various *papaya* plants.

Example 5. Transferring Mutant Allele EWSMHP into *Papaya* Line EWS-1536

When a normal female *papaya* plant, EWS-1536, was crossed with a normal hermaphrodite *papaya* plant not containing mutant allele EWSMHP, EWS-2497n, the resulting progeny segregated at approximately 52% hermaphrodite to 48% female, similar to the normal segregation as described by Storey (1938, 1953), as seen in Table 6. However, when a normal female *papaya* plant, EWS-1536, was crossed with *papaya* line EWS-2499m containing mutant allele EWSMHP of the present invention, the resulting progeny segregated at a ratio of 95.5% hermaphrodite to 4.5% female plants, indicating that mutant allele EWSMHP was transmissible and contained in the progeny.

Example 6. Transferring Mutant Allele EWSMHP into *Papaya* Line EWS-741

When a normal female *papaya* plant, EWS-741, was crossed with *papaya* line EWS-2499m containing mutant allele EWSMHP of the present invention, the resulting progeny segregated at a ratio of 96.0% hermaphrodite to 4.0% female plants, indicating that mutant allele EWSMHP is transmissible and is contained in the progeny, as shown in Table 6.

Example 7. Transferring Mutant Allele EWSMHP into *Papaya* Line EWS-775

When a normal female *papaya* plant, EWS-775, was crossed with *papaya* line EWS-2499m containing mutant allele EWSMHP of the present invention, the resulting progeny segregated at a ratio of 97.9% hermaphrodite to 2.1% female plants, indicating that mutant allele EWSMHP is transmissible and is contained in the progeny, as shown in Table 6.

Example 8. Transferring Mutant Allele EWSMHP into *Papaya* Line Maradol

When a normal female *papaya* plant, Maradol, was crossed with *papaya* line EWS-2499m containing mutant allele EWSMHP of the present invention, the resulting progeny segregated at a ratio of 95.0% hermaphrodite to 5.0% female plants, indicating that mutant allele EWSMHP is transmissible and is contained in the progeny, as shown in Table 6.

Example 9. Transferring Mutant Allele EWSMHP into *Papaya* Line EWS-2680

When a normal female *papaya* plant, EWS-2680, was crossed with *papaya* line EWS-2499m containing mutant allele EWSMHP of the present invention, the resulting progeny segregated at a ratio of 98.3% hermaphrodite to 1.7% female plants, indicating that mutant allele EWSMHP is transmissible and is contained in the progeny, as shown in Table 6.

Example 10. Transferring Mutant Allele EWSMHP into *Papaya* Line EWS-997

When a normal female *papaya* plant, EWS-997, was crossed with *papaya* line EWS-2499m containing mutant allele EWSMHP of the present invention, the resulting column 7 shows the number of female (F) $F_1$ progenies, column 8 shows the percentage of hermaphroditic $F_1$ progenies, column 9 shows the percentage of female $F_1$ progenies, column 10 shows the expected segregation ratio, column 11 shows the expected percentage of hermaphroditic $F_1$ progenies, column 12 shows the expected percentage of female $F_1$ progenies, column 13 shows the chi squared value ($\chi^2$), and column 14 shows the statistical significance where '***' indicates highly significant at P<0.001, Chi-square critical value, 1 df=6.635, and 'ns' indicates not statistically significant.

TABLE 6

| Hybrid combinations | | | | $F_1$ progenies evaluated | | | | | Expected | | | | |
|---|---|---|---|---|---|---|---|---|---|---|---|---|---|
| Female parent | Male parent | Type of cross | Transplant date | Total plants | H | F | % H | % F | segregation Ratio | % H | % F | $\chi^2$ value | Significance |
| EWS-1536 | EWS-2497n | female × normal herma | December 2011 | 198 | 103 | 95 | 52.0 | 48 | 1:1 | 50 | 50 | 0.32 | ns |
| EWS-1536 | EWS-2499m | female × mutant herma | December 2011 | 200 | 191 | 9 | 95.5 | 4.5 | 1:1 | 50 | 50 | 165.6 | *** |
| EWS-741 | EWS-2499m | female × mutant herma | December 2011 | 199 | 191 | 8 | 96.0 | 4.0 | 1:1 | 50 | 50 | 168.3 | *** |
| EWS-775 | EWS-2499m | female × mutant herma | December 2011 | 195 | 191 | 4 | 97.9 | 2.1 | 1:1 | 50 | 50 | 179.3 | *** |
| Maradol | EWS-2499m | female × mutant herma | December 2011 | 200 | 190 | 10 | 95.0 | 5.0 | 1:1 | 50 | 50 | 162.0 | *** |
| EWS-2680 | EWS-2499m | female × mutant herma | December 2011 | 179 | 176 | 3 | 98.3 | 1.7 | 1:1 | 50 | 50 | 167.2 | *** |
| EWS-997 | EWS-2499m | female × mutant herma | April 2012 | 109 | 103 | 6 | 94.5 | 5.5 | 1:1 | 50 | 50 | 86.3 | *** |
| EWS-1163 | EWS-2499m | female × mutant herma | April 2012 | 139 | 133 | 6 | 95.7 | 4.3 | 1:1 | 50 | 50 | 116.0 | *** |
| EWS-1407 | EWS-2499m | female × mutant herma | April 2012 | 68 | 66 | 2 | 97.1 | 2.9 | 1:1 | 50 | 50 | 60.2 | *** | progeny segregated at a ratio of 94.5% hermaphrodite to 5.5% female plants, indicating that mutant allele EWSMHP is transmissible and is contained in the progeny, as shown in Table 6.

Example 11. Transferring Mutant Allele EWSMHP into *Papaya* Line EWS-1163

When a normal female *papaya* plant, EWS-1163, was crossed with *papaya* line EWS-2499m containing mutant allele EWSMHP of the present invention, the resulting progeny segregated at a ratio of 95.7% hermaphrodite to 4.3% female plants, indicating that mutant allele EWSMHP is transmissible and is contained in the progeny, as shown in Table 6.

Example 12. Transferring Mutant Allele EWSMHP into *Papaya* Line EWS-1407

When a normal female *papaya* plant, EWS-1407, was crossed with *papaya* line EWS-2499m containing mutant allele EWSMHP of the present invention, the resulting progeny segregated at a ratio of 97.1% hermaphrodite to 2.9% female plants, indicating that mutant allele EWSMHP is transmissible and is contained in the progeny, as shown in Table 6.

In summary, Table 6 below shows the results of a sex segregation analysis of $F_1$ progenies derived from crosses between different sets of normal female *papaya* plants with the normal segregating herma line EWS-2497n and mutant *papaya* cultivar EWS-2499m. Table 6, column 1 shows the female plant used in the cross, column 2 shows the male parent, column 3 shows the type of cross, column 4 shows the date of transplanting, column 5 shows the total number of plants that were evaluated at flowering stage, column 6 shows the number of hermaphroditic (H) $F_1$ progenies, As shown in Table 6, all crosses with *papaya* cultivar EWS-2499m, which contains mutant allele EWSMHP, produced over 94% hermaphroditic $F_1$ progenies when crossed with a normal female, whereas a normal hermaphrodite *papaya* crossed with a normal female produces 50% hermaphroditic $F_1$ progenies. These results are clearly different from the segregation ratio observed by Chan-Tsai et al. (2003, 2006) using their all-hermaphrodite mutant line TSS No. 7 as a pollen parent, since their F1 progenies segregated to 1:1 or 50% females and 50% hermaphrodites, similar to the normal segregation as described by Storey (1938, 1953).

Further, as shown in Table 6, mutant allele EWSMHP is readily transferred between mutant *papaya* line EWS-2499m and other *papaya* plants. The presence of the EWSMHP mutant allele can readily be determined by crossing with a normal female *papaya* and analyzing the resultant $F_1$ progeny for highly hermaphroditic progenies (90-100% hermaphroditic plants and 0-10% female plants).

Further Embodiments of the Invention

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species, which are introduced into the genome using transformation or various breeding methods are referred to herein collectively as "transgenes." In some embodiments of the invention, a transgenic variant of *papaya* cultivar EWS-2499m and/or lines derived from EWS-2499m with the highly herma trait may contain at least one transgene but could contain at least 1, 2, 3, 4, 5, 6, 7, 8, 9, 10, and/or no more than 15, 14, 13, 12, 11, 10, 9, 8, 7, 6, 5, 4, 3, or 2. Over the last 15 to 20 years several methods for producing transgenic plants have been developed, and the present invention also relates to transgenic variants of the claimed *papaya* cultivar EWS-2499m.

Nucleic acids or polynucleotides refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least approximately 1000 nucleotides of sequence upstream from the 5' end of the coding region and at least approximately 200 nucleotides of sequence downstream from the 3' end of the coding region of the gene. Less common bases, such as inosine, 5-methylcytosine, 6-methyladenine, hypoxanthine and others can also be used for antisense, dsRNA and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

One embodiment of the invention is a process for producing *papaya* cultivar EWS-2499m further comprising a desired trait, said process comprising introducing a transgene that confers a desired trait to a *papaya* plant of variety EWS-2499m and/or lines derived from EWS-2499m with the highly herma trait. Another embodiment is the product produced by this process. In one embodiment the desired trait may be one or more of herbicide resistance, insect resistance, disease resistance, decreased phytate, or modified fatty acid or carbohydrate metabolism. The specific gene may be any known in the art or listed herein, including: a polynucleotide conferring resistance to imidazolinone, dicamba, sulfonylurea, glyphosate, glufosinate, triazine, benzonitrile, cyclohexanedione, phenoxy proprionic acid, and L-phosphinothricin; a polynucleotide encoding a *Bacillus thuringiensis* polypeptide; a polynucleotide encoding phytase, FAD-2, FAD-3, galactinol synthase, or a raffinose synthetic enzyme; or a polynucleotide conferring resistance to soybean cyst nematode, brown stem rot, *Phytophthora* root rot, *papaya* ringspot virus, sudden death syndrome, bacterial crown rot or die back caused by *Erwinia* spp., anthracnose caused by *Colletotrichum* spp., powdery mildew caused by *Oidium caricae*, damping off caused by *Pythium* spp., *Corynespora* leaf spot caused by *Corynespora cassiicola*, *Cercospora* black spot caused by *Cercospora papaya*, black spot caused by *Asperisporium caricae* or root knot nematode caused by *Meloidogyne* spp.

Numerous methods for plant transformation have been developed, including biological and physical plant transformation protocols. See, for example, Miki et al., "Procedures for Introducing Foreign DNA into Plants," in *Methods in Plant Molecular Biology and Biotechnology*, Glick and Thompson Eds., CRC Press, Inc., Boca Raton, pp. 67-88 (1993), and Armstrong, "The First Decade of Maize Transformation: A Review and Future Perspective," *Maydica*, 44:101-109 (1999). In addition, expression vectors and in vitro culture methods for plant cell or tissue transformation and regeneration of plants are available. See, for example, Gruber, et al., "Vectors for Plant Transformation," in *Methods in Plant Molecular Biology and Biotechnology*, Glick and Thompson Eds., CRC Press, Inc., Boca Raton, pp. 89-119 (1993).

A genetic trait which has been engineered into the genome of a particular *papaya* plant may then be moved into the genome of another variety using traditional breeding techniques that are well known in the plant breeding arts. For example, a backcrossing approach is commonly used to move a transgene from a transformed *papaya* cultivar into an already developed *papaya* cultivar, and the resulting backcross conversion plant would then comprise the transgene(s).

Various genetic elements can be introduced into the plant genome using transformation. These elements include, but are not limited to, genes, coding sequences, inducible, constitutive and tissue specific promoters, enhancing sequences, and signal and targeting sequences. For example, see the traits, genes, and transformation methods listed in U.S. Pat. No. 6,118,055.

Plant transformation involves the construction of an expression vector which will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid and can be used alone or in combination with other plasmids to provide transformed *papaya* plants using transformation methods as described below to incorporate transgenes into the genetic material of the *papaya* plant(s).

Expression Vectors for *Papaya* Transformation: Marker Genes

Expression vectors include at least one genetic marker operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Fraley, et al., *Proc. Natl. Acad. Sci. USA*, 80:4803 (1983). Another commonly used selectable marker gene is the hygromycin phosphotransferase gene which confers resistance to the antibiotic hygromycin. Vanden Elzen, et al., *Plant Mol. Biol.*, 5:299 (1985).

Additional selectable marker genes of bacterial origin that confer resistance to antibiotics include gentamycin acetyl transferase, streptomycin phosphotransferase and aminoglycoside-3'-adenyl transferase, the bleomycin resistance determinant (Hayford, et al., *Plant Physiol.*, 86:1216 (1988); Jones, et al., *Mol. Gen. Genet.*, 210:86 (1987); Svab, et al., *Plant Mol. Biol.*, 14:197 (1990); Hille, et al., *Plant Mol. Biol.*, 7:171 (1986)). Other selectable marker genes confer resistance to herbicides such as glyphosate, glufosinate, or bromoxynil (Comai, et al., *Nature*, 317:741-744 (1985); Gordon-Kamm, et al., *Plant Cell*, 2:603-618 (1990); Stalker, et al., *Science*, 242:419-423 (1988)).

Selectable marker genes for plant transformation not of bacterial origin include, for example, mouse dihydrofolate reductase, plant 5-enolpyruvylshikimate-3-phosphate synthase, and plant acetolactate synthase (Eichholtz, et al., *Somatic Cell Mol. Genet.,* 13:67 (1987); Shah, et al., *Science,* 233:478 (1986); Charest, et al., *Plant Cell Rep.,* 8:643 (1990)).

Another class of marker genes for plant transformation requires screening of presumptively transformed plant cells, rather than direct genetic selection of transformed cells, for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase, and chloramphenicol acetyltransferase (Jefferson, R. A., *Plant Mol. Biol. Rep.,* 5:387 (1987); Teeri, et al., *EMBO J.,* 8:343 (1989); Koncz, et al., *Proc. Natl. Acad. Sci. USA,* 84:131 (1987); DeBlock, et al., *EMBO J.,* 3:1681 (1984)).

In vivo methods for visualizing GUS activity that do not require destruction of plant tissue are available (Molecular Probes, Publication 2908, IMAGENE GREEN, pp. 1-4 (1993); Naleway, et al., *J. Cell Biol.,* 115:151a (1991)). However, these in vivo methods for visualizing GUS activity have not proven useful for recovery of transformed cells because of low sensitivity, high fluorescent backgrounds, and limitations associated with the use of luciferase genes as selectable markers.

More recently, a gene encoding Green Fluorescent Protein (GFP) has been utilized as a marker for gene expression in prokaryotic and eukaryotic cells (Chalfie, et al., *Science,* 263:802 (1994)). GFP and mutants of GFP may be used as screenable markers.

Expression Vectors for *Papaya* Transformation: Promoters

Genes included in expression vectors must be driven by a nucleotide sequence comprising a regulatory element (for example, a promoter). Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in a certain tissue are referred to as "tissue-specific." A "cell-type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell-type specific, and inducible promoters constitute the class of "non-constitutive" promoters. A "constitutive" promoter is a promoter that is active under most environmental conditions.

A. Inducible Promoters—An inducible promoter is operably linked to a gene for expression in *papaya*. Optionally, the inducible promoter is operably linked to a nucleotide sequence encoding a signal sequence which is operably linked to a gene for expression in *papaya*. With an inducible promoter the rate of transcription increases in response to an inducing agent.

Any inducible promoter can be used in the instant invention. See, Ward, et al., *Plant Mol. Biol.,* 22:361-366 (1993). Exemplary inducible promoters include, but are not limited to, that from the ACEI system which responds to copper (Mett, et al., *Proc. Natl. Acad. Sci. USA,* 90:4567-4571 (1993)); In2 gene from maize which responds to benzenesulfonamide herbicide safeners (Hershey, et al., *Mol. Gen. Genetics,* 227:229-237 (1991); Gatz, et al., *Mol. Gen. Genetics,* 243:32-38 (1994)); or Tet repressor from Tn10 (Gatz, et al., *Mol. Gen. Genetics,* 227:229-237 (1991)). A particularly preferred inducible promoter is a promoter that responds to an inducing agent to which plants do not normally respond. An exemplary inducible promoter is the inducible promoter from a steroid hormone gene, glucocorticoid response elements, the transcriptional activity of which is induced by a glucocorticoid hormone (Schena, et al., *Proc. Natl. Acad. Sci. USA,* 88:10421-10425 (1991)).

B. Constitutive Promoters—A constitutive promoter is operably linked to a gene for expression in *papaya* or the constitutive promoter is operably linked to a nucleotide sequence encoding a signal sequence which is operably linked to a gene for expression in *papaya*.

Many different constitutive promoters can be utilized in the instant invention. Exemplary constitutive promoters include, but are not limited to, the promoters from plant viruses such as the 35S promoter from CaMV (Odell, et al., *Nature,* 313:810-812 (1985)) and the promoters from such genes as rice actin (McElroy, et al., *Plant Cell,* 2: 163-171 (1990)); ubiquitin (Christensen, et al., *Plant Mol. Biol.,* 12:619-632 (1989); Christensen, et al., *Plant Mol. Biol.,* 18:675-689 (1992)); pEMU (Last, et al., *Theor. Appl. Genet.,* 81:581-588 (1991)); MAS (Velten, et al., *EMBO J.,* 3:2723-2730 (1984)); and maize H3 histone (Lepetit, et al., *Mol. Gen. Genetics,* 231:276-285 (1992); Atanassova, et al., *Plant Journal,* 2 (3): 291-300 (1992)). The ALS promoter, an XbaI/NcoI fragment 5' to the *Brassica napus* ALS3 structural gene (or a nucleotide sequence similarity to said XbaI/NcoI fragment), represents a particularly useful constitutive promoter. See PCT Application WO 96/30530.

C. Tissue-Specific or Tissue-Preferred Promoters—A tissue-specific promoter is operably linked to a gene for expression in *papaya*. Optionally, the tissue-specific promoter is operably linked to a nucleotide sequence encoding a signal sequence which is operably linked to a gene for expression in *papaya*. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter such as that from the phaseolin gene (Murai, et al., *Science,* 23:476-482 (1983); Sengupta-Gopalan, et al., *Proc. Natl. Acad. Sci. USA,* 82:3320-3324 (1985)); a leaf-specific and light-induced promoter such as that from cab or rubisco (Simpson, et al., *EMBO J.,* 4(11): 2723-2729 (1985); Timko, et al., *Nature,* 318:579-582 (1985)); an anther-specific promoter such as that from LAT52 (Twell, et al., *Mol. Gen. Genetics,* 217:240-245 (1989)); a pollen-specific promoter such as that from Zm13 (Guerrero, et al., *Mol. Gen. Genetics,* 244:161-168 (1993));

or a microspore-preferred promoter such as that from apg (Twell, et al., *Sex. Plant Reprod.,* 6:217-224 (1993)).

Signal Sequences for Targeting Proteins to Subcellular Compartments

Transport of a protein produced by transgenes to a subcellular compartment, such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized.

The presence of a signal sequence directs a polypeptide to either an intracellular organelle or subcellular compartment or for secretion to the apoplast. Many signal sequences are known in the art. See, for example, Becker, et al., *Plant Mol. Biol.,* 20:49 (1992); Knox, C., et al., *Plant Mol. Biol.,* 9:3-17 (1987); Lerner, et al., *Plant Physiol.,* 91:124-129 (1989); Frontes, et al., *Plant Cell,* 3:483-496 (1991); Matsuoka, et al., *Proc. Natl. Acad. Sci.,* 88:834 (1991); Gould, et al., *J. Cell. Biol.,* 108:1657 (1989); Creissen, et al., *Plant J.,* 2:129 (1991); Kalderon, et al., *Cell,* 39:499-509 (1984); Steifel, et al., *Plant Cell,* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein can then be extracted from a tissue of interest or from total biomass. Protein extraction from plant biomass can be accomplished by known methods which are discussed, for example, by Heney and Orr, *Anal. Biochem.,* 114:92-6 (1981).

According to a preferred embodiment, the transgenic plant provided for commercial production of foreign protein is a *papaya* plant. In another preferred embodiment, the biomass of interest is seed. For the relatively small number of transgenic plants that show higher levels of expression, a genetic map can be generated, primarily via conventional RFLP, PCR, and SSR analysis, which identifies the approximate chromosomal location of the integrated DNA molecule. For exemplary methodologies in this regard, see, Glick and Thompson, *Methods in Plant Molecular Biology and Biotechnology,* CRC Press, Inc., Boca Raton, 269:284 (1993). Map information concerning chromosomal location is useful for proprietary protection of a subject transgenic plant.

Wang, et al. discuss "Large Scale Identification, Mapping and Genotyping of Single-Nucleotide Polymorphisms in the Human Genome," *Science,* 280:1077-1082 (1998), and similar capabilities are becoming increasingly available for the *papaya* genome. Map information concerning chromosomal location is useful for proprietary protection of a subject transgenic plant. If unauthorized propagation is undertaken and crosses made with other germplasm, the map of the integration region can be compared to similar maps for suspect plants to determine if the latter have a common parentage with the subject plant. Map comparisons would involve hybridizations, RFLP, PCR, SSR, and sequencing, all of which are conventional techniques. SNPs may also be used alone or in combination with other techniques Likewise, by means of the present invention, plants can be genetically engineered to express various phenotypes of agronomic interest. Through the transformation of *papaya*, the expression of genes can be altered to enhance disease resistance, insect resistance, herbicide resistance, agronomic, grain quality, and other traits. Transformation can also be used to insert DNA sequences which control or help control male-sterility. DNA sequences native to *papaya*, as well as non-native DNA sequences, can be transformed into *papaya* and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing or gene suppression) is desirable for several aspects of genetic engineering in plants.

Many techniques for gene silencing are well known to one of skill in the art, including, but not limited to, knock-outs (such as by insertion of a transposable element such as mu (Vicki Chandler, The Maize Handbook, Ch. 118 (Springer-Verlag 1994)) or other genetic elements such as a FRT and Lox that are used for site specific integrations, antisense technology (see, e.g., Sheehy, et al., *PNAS USA,* 85:8805-8809 (1988); and U.S. Pat. Nos. 5,107,065, 5,453,566, and 5,759,829); co-suppression (e.g., Taylor, *Plant Cell,* 9:1245 (1997); Jorgensen, *Trends Biotech.,* 8(12):340-344 (1990); Flavell, *PNAS USA,* 91:3490-3496 (1994); Finnegan, et al., *Bio/Technology,* 12:883-888 (1994); Neuhuber, et al., *Mol. Gen. Genet.,* 244:230-241 (1994)); RNA interference (Napoli, et al., *Plant Cell,* 2:279-289 (1990); U.S. Pat. No. 5,034,323; Sharp, *Genes Dev.,* 13:139-141 (1999); Zamore, et al., *Cell,* 101:25-33 (2000); Montgomery, et al., *PNAS USA,* 95:15502-15507 (1998)), virus-induced gene silencing (Burton, et al., *Plant Cell,* 12:691-705 (2000); Baulcombe, *Curr. Op. Plant Bio.,* 2:109-113 (1999)); target-RNA-specific ribozymes (Haseloff, et al., *Nature,* 334: 585-591 (1988)); hairpin structures (Smith, et al., *Nature,* 407:319-320 (2000); WO 99/53050; WO 98/53083); MicroRNA (Aukerman & Sakai, *Plant Cell,* 15:2730-2741 (2003)); ribozymes (Steinecke, et al., *EMBO J.,* 11:1525 (1992); Perriman, et al., *Antisense Res. Dev.,* 3:253 (1993)); oligonucleotide mediated targeted modification (e.g., WO 03/076574 and WO 99/25853); Zn-finger targeted molecules (e.g., WO 01/52620, WO 03/048345, and WO 00/42219); and other methods or combinations of the above methods known to those of skill in the art.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with one or more cloned resistance genes to engineer plants that are resistant to specific pathogen strains. See, for example, Jones, et al., *Science,* 266:789 (1994) (cloning of the tomato Cf-9 gene for resistance to *Cladosporium fulvum*); Martin, et al., *Science,* 262:1432 (1993) (tomato Pto gene for resistance to *Pseudomonas syringae* pv. *tomato* encodes a protein kinase); Mindrinos, et al., *Cell,* 78:1089 (1994) (*Arabidopsis* RSP2 gene for resistance to *Pseudomonas syringae*);

McDowell & Woffenden, *Trends Biotechnol.*, 21(4):178-83 (2003); and Toyoda, et al., *Transgenic Res.*, 11 (6):567-82 (2002).

B. A gene conferring resistance to a pest, such as soybean cyst nematode. See, e.g., PCT Application WO 96/30517 and PCT Application WO 93/19181.

C. A *Bacillus thuringiensis* protein, a derivative thereof or a synthetic polypeptide modeled thereon. See, for example, Geiser, et al., *Gene*, 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995, and 31998.

D. A lectin. See, for example, Van Damme, et al., *Plant Molec. Biol.*, 24:25 (1994), who disclose the nucleotide sequences of several *Clivia miniata* mannose-binding lectin genes.

E. A vitamin-binding protein such as avidin. See, PCT Application US 93/06487, which teaches the use of avidin and avidin homologues as larvicides against insect pests.

F. An enzyme inhibitor, for example, a protease or proteinase inhibitor or an amylase inhibitor. See, for example, Abe, et al., *J. Biol. Chem.*, 262:16793 (1987) (nucleotide sequence of rice cysteine proteinase inhibitor); Huub, et al., *Plant Molec. Biol.*, 21:985 (1993) (nucleotide sequence of cDNA encoding tobacco proteinase inhibitor I); Sumitani, et al., *Biosci. Biotech. Biochem.*, 57:1243 (1993) (nucleotide sequence of *Streptomyces nitrosporeus* α-amylase inhibitor); and U.S. Pat. No. 5,494,813 (Hepher and Atkinson, issued Feb. 27, 1996).

G. An insect-specific hormone or pheromone, such as an ecdysteroid or juvenile hormone, a variant thereof, a mimetic based thereon, or an antagonist or agonist thereof. See, for example, the disclosure by Hammock, et al., *Nature*, 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, *J. Biol. Chem.*, 269:9 (1994) (expression cloning yields DNA coding for insect diuretic hormone receptor); Pratt, et al., *Biochem. Biophys. Res. Comm.*, 163:1243 (1989) (an allostatin is identified in *Diploptera puntata*); Chattopadhyay, et al., *Critical Reviews in Microbiology*, 30(1):33-54 (2004); Zjawiony, *J Nat Prod*, 67(2):300-310 (2004); Carlini & Grossi-de-Sa, *Toxicon*, 40(11):1515-1539 (2002); Ussuf, et al., *Curr Sci.*, 80(7): 847-853 (2001); Vasconcelos & Oliveira, *Toxicon*, 44(4): 385-403 (2004). See also, U.S. Pat. No. 5,266,317 to Tomalski, et al., which discloses genes encoding insect-specific, paralytic neurotoxins.

I. An insect-specific venom produced in nature by a snake, a wasp, etc. For example, see, Pang, et al., *Gene*, 116:165 (1992), for disclosure of heterologous expression in plants of a gene coding for a scorpion insectotoxic peptide.

J. An enzyme responsible for a hyperaccumulation of a monoterpene, a sesquiterpene, a steroid, hydroxamic acid, a phenylpropanoid derivative, or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See, PCT Application WO 93/02197 (Scott, et al.), which discloses the nucleotide sequence of a callase gene. DNA molecules which contain chitinase-encoding sequences can be obtained, for example, from the ATCC under Accession Nos. 39637 and 67152. See also, Kramer, et al., *Insect Biochem. Molec. Biol.*, 23:691 (1993), who teach the nucleotide sequence of a cDNA encoding tobacco hornworm chitinase, and Kawalleck, et al., *Plant Molec. Biol.*, 21:673 (1993), who provide the nucleotide sequence of the parsley ubi4-2 polyubiquitin gene, U.S. Pat. Nos. 7,145,060, 7,087, 810, and 6,563,020.

L. A molecule that stimulates signal transduction. For example, see the disclosure by Botella, et al., *Plant Molec. Biol.*, 24:757 (1994), of nucleotide sequences for mung bean calmodulin cDNA clones, and Griess, et al., *Plant Physiol.*, 104:1467 (1994), who provide the nucleotide sequence of a maize calmodulin cDNA clone.

M. A hydrophobic moment peptide. See, PCT Application WO 95/16776 and U.S. Pat. No. 5,580,852, which disclose peptide derivatives of tachyplesin which inhibit fungal plant pathogens, and PCT Application WO 95/18855 and U.S. Pat. No. 5,607,914 which teaches synthetic antimicrobial peptides that confer disease resistance.

N. A membrane permease, a channel former or a channel blocker. For example, see the disclosure of Jaynes, et al., *Plant Sci*, 89:43 (1993), of heterologous expression of a cecropin-β lytic peptide analog to render transgenic tobacco plants resistant to *Pseudomonas solanacearum*.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., *Ann. Rev. Phytopathol.*, 28:451 (1990). Coat protein-mediated resistance has been conferred upon transformed plants against alfalfa mosaic virus, cucumber mosaic virus, and tobacco mosaic virus.

P. An insect-specific antibody or an immunotoxin derived therefrom. Thus, an antibody targeted to a critical metabolic function in the insect gut would inactivate an affected enzyme, killing the insect. See, Taylor, et al., Abstract #497, Seventh Int'l Symposium on Molecular Plant-Microbe Interactions (Edinburgh, Scotland 1994) (enzymatic inactivation in transgenic tobacco via production of single-chain antibody fragments).

Q. A virus-specific antibody. See, for example, Tavladoraki, et al., *Nature*, 366:469 (1993), who show that transgenic plants expressing recombinant antibody genes are protected from virus attack.

R. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See, Lamb, et al., *Bio/Technology*, 10:1436 (1992). The cloning and characterization of a gene which encodes a bean endopolygalacturonase-inhibiting protein is described by Toubart, et al., *Plant J.*, 2:367 (1992).

S. A developmental-arrestive protein produced in nature by a plant. For example, Logemann, et al., *Bio/Technology*, 10:305 (1992), have shown that transgenic plants expressing the barley ribosome-inactivating gene have an increased resistance to fungal disease.

T. Genes involved in the Systemic Acquired Resistance (SAR) Response and/or the pathogenesis-related genes. Briggs, S., *Current Biology*, 5(2) (1995); Pieterse & Van Loon, *Curr. Opin. Plant Bio.*, 7(4):456-64 (2004); and Somssich, *Cell*, 113(7):815-6 (2003).

U. Antifungal genes. See, Cornelissen and Melchers, *Plant Physiol.*, 101:709-712 (1993); Parijs, et al., *Planta*, 183:258-264 (1991); and Bushnell, et al., *Can. J. of Plant Path.*, 20(2):137-149 (1998). See also, U.S. Pat. No. 6,875,907.

V. Detoxification genes, such as for fumonisin, beauvericin, moniliformin, and zearalenone and their structurally-related derivatives. See, for example, U.S. Pat. No. 5,792,931.

W. Cystatin and cysteine proteinase inhibitors. See, U.S. Pat. No. 7,205,453.

X. Defensin genes. See, WO 03/000863 and U.S. Pat. No. 6,911,577.

Any of the above-listed disease or pest resistance genes (A-X) can be introduced into the claimed *papaya* cultivar through a variety of means including, but not limited to, transformation and crossing.

2. Genes that Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee, et al., *EMBO J.*, 7:1241 (1988) and Mild, et al., *Theor. Appl. Genet.*, 80:449 (1990), respectively.

B. Glyphosate (resistance conferred by mutant 5-enolpyruvlshikimate-3-phosphate synthase (EPSPS) and aroA genes, respectively) and other phosphono compounds, such as glufosinate (phosphinothricin acetyl transferase (PAT) and *Streptomyces hygroscopicus* PAT bar genes), pyridinoxy or phenoxy proprionic acids, and cyclohexanediones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627,061 to Barry, et al., also describes genes encoding EPSPS enzymes. See also, U.S. Pat. Nos. 6,566,587, 6,338,961, 6,248,876, 6,040,497, 5,804,425, 5,633,435, 5,145,783, 4,971,908, 5,312,910, 5,188,642, 4,940,835, 5,866,775, 6,225,114, 6,130,366, 5,310,667, 4,535,060, 4,769,061, 5,633,448, 5,510,471, RE 36,449, RE 37,287, and 5,491,288; and International Publications EP1173580, WO 01/66704, EP1173581, and EP1173582, which are incorporated herein by reference for this purpose. Glyphosate resistance is also imparted to plants that express a gene that encodes a glyphosate oxido-reductase enzyme, as described more fully in U.S. Pat. Nos. 5,776,760 and 5,463,175, which are incorporated herein by reference for this purpose. In addition, glyphosate resistance can be imparted to plants by the over expression of genes encoding glyphosate N-acetyltransferase. See, for example, U.S. Pat. No. 7,462,481. A DNA molecule encoding a mutant aroA gene can be obtained under ATCC Accession No. 39256, and the nucleotide sequence of the mutant gene is disclosed in U.S. Pat. No. 4,769,061 to Comai. European Patent Appl. No. 0 333 033 to Kumada, et al. and U.S. Pat. No. 4,975,374 to Goodman, et al., disclose nucleotide sequences of glutamine synthetase genes which confer resistance to herbicides such as L-phosphinothricin. The nucleotide sequence of a PAT gene is provided in European Patent Appl. No. 0 242 246 to Leemans, et al. DeGreef, et al., *Bio/Technology*, 7:61 (1989) describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop are the Acc1-S1, Acc1-S2, and Acc2-S3 genes described by Marshall, et al., *Theor. Appl. Genet.*, 83:435 (1992).

C. An herbicide that inhibits photosynthesis, such as a triazine (psbA and gs+ genes) and a benzonitrile (nitrilase gene). Przbila, et al., *Plant Cell*, 3:169 (1991), describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC Accession Nos. 53435, 67441, and 67442. Cloning and expression of DNA coding for a glutathione S-transferase is described by Hayes, et al., *Biochem. J.*, 285:173 (1992).

D. Acetohydroxy acid synthase, which has been found to make plants that express this enzyme resistant to multiple types of herbicides, has been introduced into a variety of plants. See, Hattori, et al., *Mol. Gen. Genet.*, 246:419 (1995). Other genes that confer tolerance to herbicides include a gene encoding a chimeric protein of rat cytochrome P4507A1 and yeast NADPH-cytochrome P450 oxidoreductase (Shiota, et al., *Plant Physiol.*, 106:17 (1994)); genes for glutathione reductase and superoxide dismutase (Aono, et al., *Plant Cell Physiol.*, 36:1687 (1995)); and genes for various phosphotransferases (Datta, et al., *Plant Mol. Biol.*, 20:619 (1992)).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306, 6,282,837, 5,767,373, and International Publication WO 01/12825.

Any of the above listed herbicide genes (A-E) can be introduced into the claimed *papaya* cultivar through a variety of means including but not limited to transformation and crossing.

3. Genes that Confer or Contribute to a Value-Added Trait, Such as:

A. Modified fatty acid metabolism, for example, by transforming a plant with an antisense gene of stearyl-ACP desaturase to increase stearic acid content of the plant. See, Knultzon, et al., *Proc. Natl. Acad. Sci. USA*, 89:2625 (1992).

B. Decreased phytate content: 1) Introduction of a phytase-encoding gene enhances breakdown of phytate, adding more free phosphate to the transformed plant. For example, see, Van Hartingsveldt, et al., *Gene*, 127:87 (1993), for a disclosure of the nucleotide sequence of an *Aspergillus niger* phytase gene. 2) Up-regulation of a gene that reduces phytate content. In maize, this, for example, could be accomplished by cloning and then re-introducing DNA associated with one or more of the alleles, such as the LPA alleles, identified in maize mutants characterized by low levels of phytic acid, such as in Raboy, et al., *Maydica*, 35:383 (1990), and/or by altering inositol kinase activity as in WO 02/059324, U.S. Publ. No. 2003/000901, WO 03/027243, U.S. Publ. No. 2003/0079247, WO 99/05298, U.S. Pat. No. 6,197,561, U.S. Pat. No. 6,291,224, U.S. Pat. No. 6,391,348, WO 2002/059324, U.S. Publ. No. 2003/0079247, WO 98/45448, W O99/55882, and WO 01/04147.

C. Modified carbohydrate composition effected, for example, by transforming plants with a gene coding for an enzyme that alters the branching pattern of starch, or a gene altering thioredoxin, such as NTR and/or TRX (see, U.S. Pat. No. 6,531,648, which is incorporated by reference for this purpose), and/or a gamma zein knock out or mutant, such as cs27 or TUSC27 or en27 (see, U.S. Pat. No. 6,858,778, and U.S. Publ. Nos. 2005/0160488 and 2005/0204418, which are incorporated by reference for this purpose). See, Shiroza, et al., *J. Bacteriol.*, 170:810 (1988) (nucleotide sequence of *Streptococcus mutans* fructosyl-transferase gene); Steinmetz, et al., Mol. Gen. Genet., 200: 220 (1985) (nucleotide sequence of *Bacillus subtilis* levan-sucrase gene); Pen, et al., *Bio/Technology*, 10:292 (1992) (production of transgenic plants that express *Bacillus licheniformis* alpha-amylase); Elliot, et al., *Plant Molec. Biol.*, 21:515 (1993) (nucleotide sequences of tomato invertase genes); Sogaard, et al., *J. Biol. Chem.*, 268:22480 (1993) (site-directed mutagenesis of barley alpha-amylase gene); Fisher, et al., *Plant Physiol.*, 102:1045 (1993) (maize endosperm starch branching enzyme II); WO 99/10498 (improved digestibility and/or starch extraction through modification of UDP-D-xylose 4-epimerase, Fragile 1 and 2, Ref 1, HCHL, C4H); U.S. Pat. No. 6,232,529 (method of producing high oil seed by modification of starch levels (AGP)). The fatty acid modification genes mentioned above may also be used to affect starch content and/or composition through the interrelationship of the starch and oil pathways.

D. Elevated oleic acid via FAD-2 gene modification and/or decreased linolenic acid via FAD-3 gene modification. See, U.S. Pat. Nos. 6,063,947, 6,323,392, and International Publication WO 93/11245.

E. Altering conjugated linolenic or linoleic acid content, such as in WO 01/12800. Altering LEC1, AGP, Dek1, Superal1, milps, and various Ipa genes, such as Ipa1, Ipa3, hpt, or hggt. See, for example, WO 02/42424, WO 98/22604, WO 03/011015, WO 02/057439, WO 03/011015, U.S. Pat. Nos. 6,423,886, 6,197,561, 6,825,397, 7,157,621, U.S. Publ. No. 2003/0079247, and Rivera-Madrid, R., et al., *Proc. Natl. Acad. Sci.*, 92:5620-5624 (1995).

F. Altered antioxidant content or composition, such as alteration of tocopherol or tocotrienols. See, for example, U.S. Pat. Nos. 6,787,683, 7,154,029, WO 00/68393 (involving the manipulation of antioxidant levels through alteration of a phytl prenyl transferase (ppt)); WO 03/082899 (through alteration of a homogentisate geranyl geranyl transferase (hggt)).

G. Altered essential seed amino acids. See, for example, U.S. Pat. No. 6,127,600 (method of increasing accumulation of essential amino acids in seeds); U.S. Pat. No. 6,080,913 (binary methods of increasing accumulation of essential amino acids in seeds); U.S. Pat. No. 5,990,389 (high lysine); U.S. Pat. No. 5,850,016 (alteration of amino acid compositions in seeds); U.S. Pat. No. 5,885,802 (high methionine); U.S. Pat. No. 5,885,801 (high threonine); U.S. Pat. No. 6,664,445 (plant amino acid biosynthetic enzymes); U.S. Pat. No. 6,459,019 (increased lysine and threonine); U.S. Pat. No. 6,441,274 (plant tryptophan synthase beta subunit); U.S. Pat. No. 6,346,403 (methionine metabolic enzymes); U.S. Pat. No. 5,939,599 (high sulfur); U.S. Pat. No. 5,912,414 (increased methionine); U.S. Pat. No. 5,633,436 (increasing sulfur amino acid content); U.S. Pat. No. 5,559,223 (synthetic storage proteins with defined structure containing programmable levels of essential amino acids for improvement of the nutritional value of plants); U.S. Pat. No. 6,194,638 (hemicellulose); U.S. Pat. No. 7,098,381 (UD-PGdH); U.S. Pat. No. 6,194,638 (RGP); U.S. Pat. Nos. 6,399,859, 6,930,225, 7,179,955, and 6,803,498; U.S. Publ. No. 2004/0068767; WO 99/40209 (alteration of amino acid compositions in seeds); WO 99/29882 (methods for altering amino acid content of proteins); WO 98/20133 (proteins with enhanced levels of essential amino acids); WO 98/56935 (plant amino acid biosynthetic enzymes); WO 98/45458 (engineered seed protein having higher percentage of essential amino acids); WO 98/42831 (increased lysine); WO 96/01905 (increased threonine); WO 95/15392 (increased lysine); WO 01/79516; and WO 00/09706 (Ces A: cellulose synthase).

4. Genes that Control Male Sterility:

There are several methods of conferring genetic male sterility available, such as multiple mutant genes at separate locations within the genome that confer male sterility, as disclosed in U.S. Pat. Nos. 4,654,465 and 4,727,219 to Brar, et al., and chromosomal translocations as described by Patterson in U.S. Pat. Nos. 3,861,709 and 3,710,511. In addition to these methods, Albertsen, et al., U.S. Pat. No. 5,432,068, describes a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on," the promoter, which in turn allows the gene that confers male fertility to be transcribed.

A. Introduction of a deacetylase gene under the control of a tapetum-specific promoter and with the application of the chemical N-Ac-PPT. See, International Publication WO 01/29237.

B. Introduction of various stamen-specific promoters. See, International Publications WO 92/13956 and WO 92/13957.

C. Introduction of the barnase and the barstar genes. See, Paul, et al., *Plant Mol. Biol.*, 19:611-622 (1992).

For additional examples of nuclear male and female sterility systems and genes, see also, U.S. Pat. Nos. 5,859,341, 6,297,426, 5,478,369, 5,824,524, 5,850,014, and 6,265,640, all of which are hereby incorporated by reference.

5. Genes that Create a Site for Site Specific DNA Integration:

This includes the introduction of FRT sites that may be used in the FLP/FRT system and/or Lox sites that may be used in the Cre/Loxp system. See, for example, Lyznik, et al., Site-Specific Recombination for Genetic Engineering in Plants, *Plant Cell Rep*, 21:925-932 (2003) and WO 99/25821, which are hereby incorporated by reference. Other systems that may be used include the Gin recombinase of phage Mu (Maeser, et al. (1991); Vicki Chandler, The Maize Handbook, Ch. 118 (Springer-Verlag 1994)); the Pin recombinase of *E. coli* (Enomoto, et al. (1983)); and the R/RS system of the pSR1 plasmid (Araki, et al. (1992)).

6. Genes that Affect Abiotic Stress Resistance:

Genes that affect abiotic stress resistance (including but not limited to flowering, pod and seed development, enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 98/09521, and WO 99/38977 describing genes, including CBF genes and transcription factors effective in mitigating the negative effects of freezing, high salinity, and drought on plants, as well as conferring other positive effects on plant phenotype; U.S. Publ. No. 2004/0148654 and WO 01/36596, where abscisic acid is altered in plants resulting in improved plant phenotype, such as increased yield and/or increased tolerance to abiotic stress; WO 2000/006341, WO 04/090143, U.S. Pat. Nos. 7,531,723 and 6,992,237, where cytokinin expression is modified resulting in plants with increased stress tolerance, such as drought tolerance, and/or increased yield. See also, WO 02/02776, WO 2003/052063, JP 2002281975, U.S. Pat. No. 6,084,153, WO 01/64898, and U.S. Pat. Nos. 6,177,275 and 6,107,547 (enhancement of nitrogen utilization and altered nitrogen responsiveness). For ethylene alteration, see, U.S. Publ. Nos. 2004/0128719, 2003/0166197, and WO 2000/32761. For plant transcription factors or transcriptional regulators of abiotic stress, see, e.g., U.S. Publ. Nos. 2004/0098764 or 2004/0078852.

Other genes and transcription factors that affect plant growth and agronomic traits, such as yield, flowering, plant growth, and/or plant structure, can be introduced or introgressed into plants. See, e.g., WO 97/49811 (LHY), WO 98/56918 (ESD4), WO 97/10339, U.S. Pat. No. 6,573,430 (TFL), U.S. Pat. No. 6,713,663 (FT), U.S. Pat. Nos. 6,794,560, 6,307,126 (GAI), WO 96/14414 (CON), WO 96/38560, WO 01/21822 (VRN1), WO 00/44918 (VRN2), WO 99/49064 (GI), WO 00/46358 (FRI), WO 97/29123, WO 99/09174 (D8 and Rht), WO 2004/076638, and WO 004/031349 (transcription factors).

Methods for *Papaya* Transformation

Numerous methods for plant transformation have been developed including biological and physical plant transformation protocols. See, for example, Miki, et al., "Procedures for Introducing Foreign DNA into Plants," in *Methods in Plant Molecular Biology and Biotechnology*, Glick and Thompson Eds., CRC Press, Inc., Boca Raton, pp. 67-88 (1993). In addition, expression vectors and in-vitro culture methods for plant cell or tissue transformation and regeneration of plants are available. See, for example, Gruber, et al., "Vectors for Plant Transformation," in *Methods in Plant Molecular Biology and Biotechnology*, Glick and Thompson Eds., CRC Press, Inc., Boca Raton, pp. 89-119 (1993).

A. *Agrobacterium*-mediated Transformation—One method for introducing an expression vector into plants is based on the natural transformation system of *Agrobacterium*. See, for example, Horsch, et al., *Science*, 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.*, 10:1 (1991). Descriptions of *Agrobacterium* vector systems and methods for *Agrobacterium*-mediated gene transfer are provided by Gruber, et al., supra, Miki, et al., supra, and Moloney, et al., *Plant Cell Reports*, 8:238 (1989). See also, U.S. Pat. No. 5,563,055 (Townsend and Thomas), issued Oct. 8, 1996.

B. Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation where DNA is carried on the surface of microprojectiles measuring 1 to 4 µm. The expression vector is introduced into plant tissues with a biolistic device that accelerates the microprojectiles to speeds of 300 to 600 m/s which is sufficient to penetrate plant cell walls and membranes. Sanford, et al., *Part. Sci. Technol.*, 5:27 (1987); Sanford, J. C., *Trends Biotech.*, 6:299 (1988); Klein, et al., *Bio/Tech.*, 6:559-563 (1988); Sanford, J. C., *Physiol Plant*, 7:206 (1990); Klein, et al., *Biotechnology*, 10:268 (1992). See also, U.S. Pat. No. 5,015,580 (Christou, et al.), issued May 14, 1991 and U.S. Pat. No. 5,322,783 (Tomes, et al.), issued Jun. 21, 1994.

Another method for physical delivery of DNA to plants is sonication of target cells. Zhang, et al., *Bio/Technology*, 9:996 (1991). Alternatively, liposome and spheroplast fusion have been used to introduce expression vectors into plants. Deshayes, et al., *EMBO J.*, 4:2731 (1985); Christou, et al., *Proc Natl. Acad. Sci. USA*, 84:3962 (1987). Direct uptake of DNA into protoplasts using $CaCl_2$ precipitation, polyvinyl alcohol or poly-L-ornithine have also been reported. Hain, et al., *Mol. Gen. Genet.*, 199:161 (1985) and Draper, et al., *Plant Cell Physiol.*, 23:451 (1982). Electroporation of protoplasts and whole cells and tissues have also been described (Donn, et al., In Abstracts of VIIth International Congress on Plant Cell and Tissue Culture IAPTC, A2-38, p. 53 (1990); D'Halluin, et al., *Plant Cell*, 4:1495-1505 (1992); and Spencer, et al., *Plant Mol. Biol.*, 24:51-61 (1994)).

Following transformation of *papaya* target tissues, expression of the above-described selectable marker genes allows for preferential selection of transformed cells, tissues, and/or plants, using regeneration and selection methods well known in the art.

The foregoing methods for transformation would typically be used for producing a transgenic variety. The transgenic variety could then be crossed with another (non-transformed or transformed) variety in order to produce a new transgenic variety. Alternatively, a genetic trait that has been engineered into a particular *papaya* line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties that do not contain that gene. As used herein, "crossing" can refer to a simple x by y cross or the process of backcrossing depending on the context.

Genetic Marker Profile Through SSR and First Generation Progeny

In addition to phenotypic observations, a plant can also be identified by its genotype. The genotype of a plant can be characterized through a genetic marker profile which can identify plants of the same variety, or a related variety, or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) (which are also referred to as Microsatellites), and Single Nucleotide Polymorphisms (SNPs). For example, see, Cregan, et al., "An Integrated Genetic Linkage Map of the Soybean Genome," *Crop Science*, 39:1464-1490 (1999) and Berry, et al., "Assessing Probability of Ancestry Using Simple Sequence Repeat Profiles: Applications to Maize Inbred Lines and Soybean Varieties," *Genetics*, 165:331-342 (2003), each of which are incorporated by reference herein in their entirety.

Particular markers used for these purposes are not limited to any particular set of markers, but are envisioned to include any type of marker and marker profile which provides a means of distinguishing varieties. One method of comparison is to use only homozygous loci for *papaya* cultivar EWS-2499m.

In addition to being used for identification of *papaya* cultivar EWS-2499m, and plant parts and plant cells of *papaya* cultivar EWS-2499m, the genetic profile may be used to identify a *papaya* plant produced through the use of *papaya* cultivar EWS-2499m or to verify a pedigree for progeny plants produced through the use of *papaya* cultivar EWS-2499m. The genetic marker profile is also useful in breeding and developing backcross conversions.

The present invention comprises a *papaya* plant characterized by molecular and physiological data obtained from the representative sample of said variety deposited with the American Type Culture Collection (ATCC). Further provided by the invention is a *papaya* plant formed by the combination of the disclosed *papaya* plant or plant cell with another *papaya* plant or cell and comprising the homozygous alleles of the variety.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by polymerase chain reaction (PCR), thereby eliminating the need for labor-intensive Southern hybridization. PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing varieties it is preferable if all SSR profiles are performed in the same lab.

The SSR profile of *papaya* plant EWS-2499m can be used to identify plants comprising *papaya* cultivar EWS-2499m as a parent, since such plants will comprise the same homozygous alleles as *papaya* cultivar EWS-2499m. Because the *papaya* cultivar is essentially homozygous at all relevant loci, most loci should have only one type of allele present. In contrast, a genetic marker profile of an $F_1$ progeny should be the sum of those parents, e.g., if one parent was homozygous for allele x at a particular locus, and the other parent homozygous for allele y at that locus, then the $F_1$ progeny will be xy (heterozygous) at that locus. Subsequent generations of progeny produced by selection and breeding are expected to be of genotype x (homozygous), y (homozygous), or xy (heterozygous) for that locus position. When the $F_1$ plant is selfed or sibbed for successive filial generations, the locus should be either x or y for that position.

In addition, plants and plant parts substantially benefiting from the use of *papaya* cultivar EWS-2499m in their development, such as *papaya* cultivar EWS-2499m comprising a backcross conversion, transgene, or genetic sterility factor, may be identified by having a molecular marker profile with a high percent identity to *papaya* cultivar EWS-2499m. Such a percent identity might be 95%, 96%, 97%, 98%, 99%, 99.5%, or 99.9% identical to *papaya* cultivar EWS-2499m.

The SSR profile of *papaya* cultivar EWS-2499m can also be used to identify essentially derived varieties and other progeny varieties developed from the use of *papaya* cultivar EWS-2499m, as well as cells and other plant parts thereof. Progeny plants and plant parts produced using *papaya* cultivar EWS-2499m may be identified by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% genetic contribution from *papaya* cultivar, as measured by either percent identity or percent similarity. Such progeny may be further characterized as being within a pedigree distance of *papaya* cultivar EWS-2499m, such as within 1, 2, 3, 4, or 5 or less cross-pollinations to a *papaya* plant other than *papaya* cultivar EWS-2499m or a plant that has *papaya* cultivar EWS-2499m as a progenitor. Unique molecular profiles may be identified with other molecular tools such as SNPs and RFLPs.

While determining the SSR genetic marker profile of the plants described supra, several unique SSR profiles may also be identified which did not appear in either parent of such plant. Such unique SSR profiles may arise during the breeding process from recombination or mutation. A combination of several unique alleles provides a means of identifying a plant variety, an $F_1$ progeny produced from such variety, and progeny produced from such variety.

Single-Gene Conversions

When the term "*papaya* plant" is used in the context of the present invention, this also includes any single gene conversions of that variety. The term single gene converted plant as used herein refers to those *papaya* plants which are developed by a plant breeding technique called backcrossing wherein essentially all of the desired morphological and physiological characteristics of a variety are recovered in addition to the single gene transferred into the variety via the backcrossing technique. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, or more times to the recurrent parent. The parental *papaya* plant that contributes the gene for the desired characteristic is termed the nonrecurrent or donor parent. This terminology refers to the fact that the nonrecurrent parent is used one time in the backcross protocol and therefore does not recur. The parental *papaya* plant to which the gene or genes from the nonrecurrent parent are transferred is known as the recurrent parent as it is used for several rounds in the backcrossing protocol (Poehlman & Sleper (1994); Fehr, Principles of Cultivar Development, pp. 261-286 (1987)). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a *papaya* plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic. Examples of these traits include, but are not limited to, male sterility, waxy starch, herbicide resistance, resistance for bacterial, fungal, or viral disease, insect resistance, male fertility, enhanced nutritional quality, industrial usage, yield stability, and yield enhancement. These genes are generally inherited through the nucleus. Several of these single gene traits are described in U.S. Pat. Nos. 5,959,185, 5,973,234, and 5,977,445, the disclosures of which are specifically hereby incorporated by reference.

Introduction of a New Trait or Locus into *Papaya* Cultivar EWS-2499m

Variety EWS-2499m and *papaya* plants containing mutant allele designated EWSMHP, which confers production of highly hermaphroditic progenies upon selfing of its hermaphrodite plants and also production of highly hermaphroditic $F_1$ progenies when crossed with normal female and normal hermaphrodite *papaya* plants, represent a new base genetic variety into which a new locus or trait may be introgressed. Direct transformation and backcrossing represent two important methods that can be used to accomplish such an introgression. The term backcross conversion and single locus conversion are used interchangeably to designate the product of a backcrossing program.

Backcross Conversions of *Papaya* Cultivar EWS-2499m

A backcross conversion of *papaya* cultivar EWS-2499m or *papaya* plants containing mutant allele EWSMHP occurs when DNA sequences are introduced through backcrossing with *papaya* cultivar EWS-2499m utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses, and the like. Molecular marker assisted breeding or selection may be utilized to reduce the number of backcrosses necessary to achieve the backcross conversion. For example, see, Openshaw, S. J., et al., Marker-assisted Selection in Backcross Breeding, *Proceedings Symposium of the Analysis of Molecular Data*, Crop Science Society of America, Corvallis, Oreg. (August 1994), where it is demonstrated that a backcross conversion can be made in as few as two backcrosses.

The complexity of the backcross conversion method depends on the type of trait being transferred (single genes or closely linked genes as compared to unlinked genes), the level of expression of the trait, the type of inheritance (cytoplasmic or nuclear), and the types of parents included in the cross. It is understood by those of ordinary skill in the art that for single gene traits that are relatively easy to classify, the backcross method is effective and relatively easy to manage. (See, Hallauer, et al., *Corn and Corn Improvement*, Sprague and Dudley, Third Ed. (1998)). Desired traits that may be transferred through backcross conversion include, but are not limited to, sterility (nuclear and cytoplasmic), fertility restoration, nutritional enhancements, drought tolerance, nitrogen utilization, altered fatty acid profile, low phytate, industrial enhancements, disease resistance (bacterial, fungal, or viral), insect resistance, and herbicide resistance. In addition, an introgression site itself, such as an FRT site, Lox site, or other site specific integration site, may be inserted by backcrossing and utilized for direct insertion of one or more genes of interest into a specific plant variety. In some embodiments of the invention, the number of loci that may be backcrossed into *papaya* cultivar EWS-2499m is at least 1, 2, 3, 4, or 5, and/or no more than 6, 5, 4, 3, or 2. A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of site specific integration system allows for the integration of multiple genes at the converted loci.

The backcross conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype of the recurrent parent. The backcross is a form of inbreeding, and the features of the recurrent parent are automatically recovered after successive backcrosses. Poehlman, *Breeding Field Crops*, p. 204 (1987). Poehlman suggests from one to four or more backcrosses, but as noted above, the number of backcrosses necessary can be reduced with the use of molecular markers. Other factors, such as a genetically similar donor parent, may also reduce the number of backcrosses necessary. As noted by Poehlman, backcrossing is easiest for simply inherited, dominant, and easily recognized traits.

One process for adding or modifying a trait or locus in *papaya* cultivar EWS-2499m or *papaya* plants containing mutant allele EWSMHP comprises crossing *papaya* cultivar EWS-2499m plants grown from *papaya* cultivar EWS-2499m seed with plants of another *papaya* cultivar that comprise the desired trait or locus, selecting $F_1$ progeny plants that comprise the desired trait or locus to produce selected $F_1$ progeny plants, crossing the selected progeny plants with the *papaya* cultivar EWS-2499m plants to produce backcross progeny plants, selecting for backcross progeny plants that have the desired trait or locus and the morphological characteristics of *papaya* cultivar EWS-2499m to produce selected backcross progeny plants, and backcrossing to *papaya* cultivar EWS-2499m three or more times in succession to produce selected fourth or higher backcross progeny plants that comprise said trait or locus. The modified *papaya* cultivar EWS-2499m may be further characterized as having the physiological and morphological characteristics of *papaya* cultivar EWS-2499m listed in Table 4 as determined at the 5% significance level when grown in the same environmental conditions and/or may be characterized by percent similarity or identity to *papaya* cultivars containing mutant allele EWSMHP as determined by SSR markers. The above method may be utilized with fewer backcrosses in appropriate situations, such as when the donor parent is highly related or markers are used in the selection step. Desired traits that may be used include those nucleic acids known in the art, some of which are listed herein, that will affect traits through nucleic acid expression or inhibition. Desired loci include the introgression of FRT, Lox, and other sites for site specific integration, which may also affect a desired trait if a functional nucleic acid is inserted at the integration site.

In addition, the above process and other similar processes described herein may be used to produce first generation progeny *papaya* seed by adding a step at the end of the process that comprises crossing *papaya* cultivar EWS-2499m with the introgressed trait or locus with a different *papaya* plant and harvesting the resultant first generation progeny *papaya* seed.

Tissue Culture

Further reproduction of the variety can occur by tissue culture and regeneration. Tissue culture of various tissues of papayas and regeneration of plants therefrom is well known and widely published. For example, reference may be had to Komatsuda, T., et al., *Crop Sci.*, 31:333-337 (1991); Stephens, P. A., et al., *Theor. Appl. Genet.*, 82:633-635 (1991); Komatsuda, T., et al., *Plant Cell, Tissue and Organ Culture*, 28:103-113 (1992); Dhir, S., et al., *Plant Cell Reports*, 11:285-289 (1992); Pandey, P., et al., *Japan J. Breed.*, 42:1-5 (1992); and Shetty, K., et al., *Plant Science*, 81:245-251 (1992); as well as U.S. Pat. No. 5,024,944, issued Jun. 18, 1991 to Collins, et al. and U.S. Pat. No. 5,008,200, issued Apr. 16, 1991 to Ranch, et al. Thus, another aspect of this invention is to provide cells which upon growth and differentiation produce *papaya* plants having the physiological and morphological characteristics of *papaya* cultivar EWS-2499m or *papaya* plants having the EWSMHP mutant allele.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, petioles, leaves, stems, roots, root tips, anthers, pistils, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques, the disclosures of which are incorporated herein by reference.

Using *Papaya* Cultivar EWS-2499m to Develop Other *Papaya* Varieties

*Papaya* varieties such as *papaya* cultivar EWS-2499m are typically developed for use in seed and fruit production. However, *papaya* varieties containing mutant allele EWSMHP such as *papaya* cultivar EWS-2499m also provide a source of breeding material that may be used to develop new *papaya* varieties. Plant breeding techniques known in the art and used in a *papaya* plant breeding program include, but are not limited to, recurrent selection, bulk selection, mass selection, backcrossing, pedigree breeding, open pollination breeding, restriction fragment length polymorphism enhanced selection, genetic marker enhanced selection, making double haploids, and transformation. Often combinations of these techniques are used. The development of *papaya* varieties in a plant breeding program requires, in general, the development and evaluation of homozygous varieties. There are many analytical methods available to evaluate a new variety. The oldest and most traditional method of analysis is the observation of phenotypic traits, but genotypic analysis may also be used.

Additional Breeding Methods

This invention is directed to methods for producing a *papaya* plant by crossing a first parent *papaya* plant with a second parent *papaya* plant wherein either the first or second parent *papaya* plant is a *papaya* plant containing mutant allele EWSMHP, such as *papaya* variety EWS-2499m. The other parent may be any other *papaya* plant, such as a *papaya* plant that is part of a synthetic or natural population. Any such methods using a *papaya* plant containing mutant allele EWSMHP, such as *papaya* cultivar EWS-2499m are part of this invention: selfing, sibbing, backcrosses, mass selection, pedigree breeding, bulk selection, hybrid production, crosses to populations, and the like. These methods are well known in the art and some of the more commonly used breeding methods are described below. Descriptions of breeding methods can be found in one of several reference books (e.g., Allard, Principles of Plant Breeding (1960); Simmonds, Principles of Crop Improvement (1979); Sneep, et al. (1979); Fehr, "Breeding Methods for Cultivar Development," Chapter 7, Soybean Improvement, Production and Uses, 2.sup.nd ed., Wilcox editor (1987)).

The following describes breeding methods that may be used with a *papaya* plant containing mutant allele EWSMHP, such as *papaya* cultivar EWS-2499m in the development of further *papaya* plants. One such embodiment is a method for developing a cultivar EWS-2499m progeny *papaya* plant in a *papaya* plant breeding program comprising: obtaining the *papaya* plant, or a part thereof, of cultivar EWS-2499m, utilizing said plant, or plant part, as a source of breeding material, and selecting a *papaya* cultivar EWS-2499m progeny plant with molecular markers in common with cultivar EWS-2499m and/or with morphological and/or physiological characteristics selected from the characteristics listed in Table 4. Breeding steps that may be used in the *papaya* plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of *papaya* containing mutant allele EWSMHP, such as *papaya* cultivar EWS-2499m progeny *papaya* plants, comprising crossing cultivar EWS-2499m with another *papaya* plant, thereby producing a population of *papaya* plants which, on average, derive 50% of their alleles from *papaya* cultivar EWS-2499m. A plant of this population may be selected and repeatedly selfed or sibbed with a *papaya* cultivar resulting from these successive filial generations. One embodiment of this invention is the *papaya* cultivar produced by this method and that has obtained at least 50% of its alleles from *papaya* cultivar EWS-2499m.

One of ordinary skill in the art of plant breeding would know how to evaluate the traits of two plant varieties to determine if there is no significant difference between the two traits expressed by those varieties. For example, see, Fehr and Walt, *Principles of Cultivar Development*, pp. 261-286 (1987). Thus the invention includes *papaya* cultivar EWS-2499m progeny *papaya* plants comprising a combination of at least two cultivar EWS-2499m traits selected from the group consisting of those listed in Table 4 or the cultivar EWS-2499m combination of traits listed in the Summary of the Invention, so that said progeny *papaya* plant is not significantly different for said traits than *papaya* cultivar EWS-2499m as determined at the 5% significance level when grown in the same environmental conditions. Using techniques described herein, molecular markers may be used to identify said progeny plant as a *papaya* cultivar EWS-2499m progeny plant. Mean trait values may be used to determine whether trait differences are significant, and preferably the traits are measured on plants grown under the same environmental conditions. Once such a variety is developed, its value is substantial since it is important to advance the germplasm base as a whole in order to maintain or improve traits such as yield, disease resistance, pest resistance, and plant performance in extreme environmental conditions.

Progeny of *papaya* cultivar EWS-2499m may also be characterized through their filial relationship with *papaya* cultivar EWS-2499m, as for example, being within a certain number of breeding crosses of *papaya* cultivar EWS-2499m. A breeding cross is a cross made to introduce new genetics into the progeny, and is distinguished from a cross, such as a self or a sib cross, made to select among existing genetic alleles. The lower the number of breeding crosses in the pedigree, the closer the relationship between *papaya* cultivar EWS-2499m and its progeny. For example, progeny produced by the methods described herein may be within 1, 2, 3, 4, or 5 breeding crosses of *papaya* cultivar EWS-2499m.

As used herein, the term "plant" includes plant cells, plant protoplasts, plant cell tissue cultures from which *papaya* plants can be regenerated, plant calli, plant clumps, and plant cells that are intact in plants or parts of plants, such as embryos, pollen, ovules, flowers, pods, leaves, roots, root tips, anthers, cotyledons, hypocotyls, meristematic cells, stems, pistils, petiole, and the like.

Pedigree Breeding

Pedigree breeding starts with the crossing of two genotypes, such as a *papaya* plant containing mutant allele EWSMHP, such as *papaya* cultivar EWS-2499m and another *papaya* cultivar having one or more desirable characteristics that is lacking or which complements *papaya* cultivar EWS-2499m. If the two original parents do not provide all the desired characteristics, other sources can be included in the breeding population. In the pedigree method, superior plants are selfed and selected in successive filial generations. In the succeeding filial generations, the heterozygous condition gives way to homogeneous varieties as a result of self-pollination and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$; etc. After a sufficient amount of inbreeding, successive filial generations will serve to increase seed of the developed variety. Preferably, the developed variety comprises homozygous alleles at about 95% or more of its loci.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent, but at the same time retain many components of the nonrecurrent parent by stopping the backcrossing at an early stage and proceeding with selfing and selection. For example, a *papaya* cultivar may be crossed with another variety to produce a first generation progeny plant. The first generation progeny plant may then be backcrossed to one of its parent varieties to create a $BC_1$ or $BC_2$. Progeny are selfed and selected so that the newly developed variety has many of the attributes of the recurrent parent and yet several of the desired attributes of the nonrecurrent parent. This approach leverages the value and strengths of the recurrent parent for use in new *papaya* varieties.

Therefore, an embodiment of this invention is a method of making a backcross conversion of a *papaya* plant containing mutant allele EWSMHP, such as *papaya* cultivar EWS-2499m, comprising the steps of crossing a plant of *papaya* cultivar EWS-2499m with a donor plant comprising a desired trait, selecting an $F_1$ progeny plant comprising the desired trait, and backcrossing the selected $F_1$ progeny plant to a plant of *papaya* cultivar EWS-2499m. This method may further comprise the step of obtaining a molecular marker profile of *papaya* cultivar EWS-2499m and using the molecular marker profile to select for a progeny plant with the desired trait and the molecular marker profile of *papaya* cultivar EWS-2499m. In one embodiment, the desired trait is a mutant gene or transgene present in the donor parent.

Recurrent Selection and Mass Selection

Recurrent selection is a method used in a plant breeding program to improve a population of plants. *Papaya* cultivar EWS-2499m is suitable for use in a recurrent selection program. The method entails individual plants cross pollinating with each other to form progeny. The progeny are grown and the superior progeny selected by any number of selection methods, which include individual plant, half-sib progeny, full-sib progeny, and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic cultivar. A synthetic cultivar is the resultant progeny formed by the intercrossing of several selected varieties.

Mass selection is a useful technique when used in conjunction with molecular marker enhanced selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk, and then using a sample of the seed harvested in bulk to plant the next generation. Also, instead of self pollination, directed pollination could be used as part of the breeding program.

Mutation Breeding

Mutation breeding is another method of introducing new traits into a *papaya* plant containing mutant allele EWSMHP, such as *papaya* cultivar EWS-2499m. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil)), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in Fehr, "Principles of Cultivar Development," Macmillan Publishing Company (1993). Mutation breeding also includes the use of techniques such as Targeting Induced Local Lesions IN Genomes (TILLING), Transcription Activator-Like Effectors Nucleases (TALENs) and Clustered Regulatory Interspaced Short Palindromic Repeats (CRISPRs). In addition, mutations created in other *papaya* plants may be used to produce a backcross conversion of *papaya* cultivar EWS-2499m that comprises such mutation.

Breeding with Molecular Markers

Molecular markers, which includes markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), and Single Nucleotide Polymorphisms (SNPs), may be used in plant breeding methods utilizing *papaya* cultivar EWS-2499m.

Isozyme Electrophoresis and RFLPs have been widely used to determine genetic composition. Shoemaker and Olsen, Molecular Linkage Map of Soybean (*Glycine max* L. Merr.), pp. 6.131-6.138 (1993). In S. J. O'Brien (ed.), *Genetic Maps: Locus Maps of Complex Genomes*, Cold Spring Harbor Laboratory Press, Cold Spring Harbor, N.Y., developed a molecular genetic linkage map that consisted of 25 linkage groups with about 365 RFLP, 11 RAPD (random amplified polymorphic DNA), 3 classical markers, and 4 isozyme loci. See also, Shoemaker, R. C., 1994 RFLP Map of Soybean, pp. 299-309; In R. L. Phillips and I. K. Vasil (ed.), *DNA-based markers in plants*, Kluwer Academic Press Dordrecht, the Netherlands.

SSR technology is currently the most efficient and practical marker technology. More marker loci can be routinely used, and more alleles per marker locus can be found, using SSRs in comparison to RFLPs. For example, Diwan and Cregan described a highly polymorphic microsatellite loci in soybean with as many as 26 alleles. (Diwan, N., and Cregan. P. B., Automated sizing of fluorescent-labeled simple sequence repeat (SSR) markers to assay genetic variation in Soybean, *Theor. Appl. Genet.*, 95:220-225 (1997). Single Nucleotide Polymorphisms may also be used to identify the unique genetic composition of the invention and progeny varieties retaining that unique genetic composition. Various molecular marker techniques may be used in combination to enhance overall resolution.

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Production of Double Haploids

The production of double haploids can also be used for the development of plants with a homozygous phenotype in the breeding program. For example, a *papaya* plant for which *papaya* cultivar EWS-2499m is a parent can be used to produce double haploid plants. Double haploids are produced by the doubling of a set of chromosomes (1 N) from a heterozygous plant to produce a completely homozygous individual. For example, see, Wan, et al., "Efficient Production of Doubled Haploid Plants Through Colchicine Treatment of Anther-Derived Maize Callus," *Theoretical and Applied Genetics*, 77:889-892 (1989) and U.S. Pat. No. 7,135,615. This can be advantageous because the process omits the generations of selfing needed to obtain a homozygous plant from a heterozygous source.

Haploid induction systems have been developed for various plants to produce haploid tissues, plants and seeds. The haploid induction system can produce haploid plants from any genotype by crossing a selected line (as female) with an inducer line. Such inducer lines for maize include Stock 6 (Coe, *Am. Nat.*, 93:381-382 (1959); Sharkar and Coe, *Genetics*, 54:453-464 (1966); KEMS (Deimling, Roeber, and Geiger, *Vortr. Pflanzenzuchtg*, 38:203-224 (1997); or KMS and ZMS (Chalyk, Bylich & Chebotar, *MNL*, 68:47 (1994); Chalyk & Chebotar, *Plant Breeding*, 119:363-364 (2000)); and indeterminate gametophyte (ig) mutation (Kermicle, *Science*, 166:1422-1424 (1969). The disclosures of which are incorporated herein by reference.

Methods for obtaining haploid plants are also disclosed in Kobayashi, M., et al., Journ. of Heredity, 71(1):9-14 (1980); Pollacsek, M., Agronomie (Paris) 12(3):247-251 (1992); Cho-Un-Haing, et al., *Journ. of Plant Biol.*, 39(3):185-188 (1996); Verdoodt, L., et al., 96(2):294-300 (February 1998); Genetic Manipulation in Plant Breeding, Proceedings International Symposium Organized by EUCARPIA, Berlin, Germany (Sep. 8-13, 1985); Chalyk, et al., *Maize Genet Coop*., Newsletter 68:47 (1994).

Thus, an embodiment of this invention is a process for making a substantially homozygous *papaya* cultivar EWS-2499m progeny plant by producing or obtaining a seed from the cross of *papaya* cultivar EWS-2499m and another *papaya* plant, or a cross between a *papaya* plant containing mutant allele EWSMHP and another *papaya* plant and applying double haploid methods to the $F_1$ seed or $F_1$ plant or to any successive filial generation. Based on studies in maize, such methods would decrease the number of generations required to produce a variety with similar genetics or characteristics to *papaya* cultivar EWS-2499m. See, Bernardo, R. and Kahler, A. L., *Theor. Appl. Genet.*, 102:986-992 (2001).

In particular, a process of making seed retaining the molecular marker profile of *papaya* cultivar EWS-2499m is contemplated, such process comprising obtaining or producing $F_1$ seed for which *papaya* cultivar EWS-2499m is a parent, inducing doubled haploids to create progeny without the occurrence of meiotic segregation, obtaining the molecular marker profile of *papaya* cultivar EWS-2499m, and selecting progeny that retain the molecular marker profile of *papaya* cultivar EWS-2499m.

Descriptions of other breeding methods that are commonly used for different traits and crops can be found in one of several reference books (e.g., Allard (1960); Simmonds (1979); Sneep, et al. (1979); Fehr (1987)).

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

DEPOSIT INFORMATION

A deposit of the Hortigenetics Research (S.E. Asia) Ltd. proprietary *papaya* seed EWS-2499m containing mutant allele EWSMHP of the invention disclosed above and recited in the appended claims has been made with the American Type Culture Collection (ATCC), 10801 University Boulevard, Manassas, Va. 20110. The date of deposit was Jan. 20, 2014. The deposit of 2,500 seeds was taken from the same deposit maintained by Hortigenetics Research (S.E. Asia) Ltd. since prior to the filing date of this application. All restrictions will be irrevocably removed upon granting of a patent, and the deposit is intended to meet all of the requirements of 37 C.F.R. § § 1.801-1.809. The ATCC Accession Number is PTA-120861. The deposit will be maintained in the depository for a period of thirty years, or five years after the last request, or for the enforceable life of the patent, whichever is longer, and will be replaced as necessary during that period.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions, and sub-combinations as are within their true spirit and scope.

What is claimed is:

1. A seed of *papaya* cultivar EWS-2499m, wherein a representative sample of seed of said cultivar is deposited under ATCC Accession No. PTA-120861.

2. A *papaya* plant, or a part thereof, produced by growing the seed of claim 1.

3. A tissue culture produced from protoplasts or cells from the plant of claim 2, wherein said cells or protoplasts are produced from a plant part selected from the group consisting of leaf, pollen, ovule, embryo, cotyledon, hypocotyl, meristematic cell, root, root tip, pistil, anther, flower, seed, shoot, stem, fruit and petiole.

4. A *papaya* plant regenerated from the tissue culture of claim 3, wherein the plant has all of the morphological and physiological characteristics of *papaya* cultivar EWS-2499m.

5. A method for producing an $F_1$ *papaya* seed, said method comprising crossing two *papaya* plants and harvesting the resultant *papaya* seed, wherein at least one *papaya* plant is the *papaya* plant of claim 2.

6. An $F_1$ *papaya* seed produced by the method of claim 5.

7. An $F_1$ *papaya* plant, or a part thereof, produced by growing said seed of claim 6.

8. The method of claim 5, wherein at least one of said *papaya* plants is transgenic.

9. A method of producing an herbicide resistant *papaya* plant, wherein said method comprises introducing a gene conferring herbicide resistance into the plant of claim 2.

10. A herbicide resistant *papaya* plant produced by the method of claim 9, wherein the gene confers resistance to a herbicide selected from the group consisting of glyphosate, sulfonylurea, imidazolinone, dicamba, glufosinate, phenoxy proprionic acid, L-phosphinothricin, cyclohexone, cyclohexanedione, triazine, 2,4-Dichlorophenoxyacetic acid, hydroxyphenyl-pyruvate dioxygenase (HPPD) inhibitors and benzonitrile.

11. A method of producing a pest or insect resistant *papaya* plant, wherein said method comprises introducing a gene conferring pest or insect resistance into the *papaya* plant of claim 2.

12. A pest or insect resistant *papaya* plant produced by the method of claim 11.

13. The *papaya* plant of claim 12, wherein the gene encodes a *Bacillus thuringiensis* (Bt) endotoxin.

14. A method of producing a disease resistant *papaya* plant, wherein said method comprises introducing a gene which confers disease resistance into the *papaya* plant of claim 2.

15. A disease resistant *papaya* plant produced by the method of claim 14.

16. A method of producing a commodity plant product, comprising obtaining the plant of claim 2, or a part thereof, and producing the commodity plant product from said plant or plant part thereof.

17. A method of producing a mutant *papaya* plant comprising contacting the plant of claim 2 or a part thereof with a mutagen and selecting for plants having at least one new or altered trait.

18. A method of introducing a desired trait into *papaya* cultivar EWS-2499m, wherein the method comprises:
(a) crossing a EWS-2499m plant, wherein a representative sample of seed of said cultivar is deposited under ATCC Accession No. PTA-120861, with a plant of another *papaya* cultivar that comprises a desired trait, wherein said desired trait is selected from the group consisting of male sterility, herbicide resistance, insect resistance, abiotic stress tolerance, modified fatty acid metabolism, modified carbohydrate metabolism, modified seed yield, modified oil percent, modified protein percent, modified fruit yield, enhanced nutritional quality, improved processing characteristics, modified iron-deficiency chlorosis and resistance to bacterial disease, fungal disease and viral disease;

(b) selecting one or more progeny plants that have the desired trait;

(c) backcrossing the selected progeny plants with *papaya* cultivar EWS-2499m to produce backcross progeny plants;

(d) selecting for backcross progeny plants that have the desired trait; and (e) repeating steps (c) and (d) two or more times in succession to produce selected third or higher backcross progeny plants that comprise the desired trait.

19. A *papaya* plant produced by the method of claim 18, wherein the plant has the desired trait and otherwise all of the physiological and morphological characteristics of *papaya* cultivar EWS-2499m listed in Table 4.

20. The *papaya* plant of claim 19, wherein the desired trait is herbicide resistance and the resistance is conferred to an herbicide selected from the group consisting of imidazolinone, dicamba, cyclohexanedione, sulfonylurea, glyphosate, glufosinate, phenoxy proprionic acid, L-phosphinothricin, triazine, 2,4-Dichlorophenoxyacetic acid, hydroxyphenylpyruvate dioxygenase (HPPD) inhibitors and benzonitrile.

21. The *papaya* plant of claim 19, wherein the desired trait is insect resistance and the insect resistance is conferred by a gene encoding a *Bacillus thuringiensis* endotoxin.

22. The *papaya* plant of claim 19, wherein the desired trait is disease resistance.

* * * * *